US007935823B2

(12) United States Patent
Aksinenko et al.

(10) Patent No.: US 7,935,823 B2
(45) Date of Patent: *May 3, 2011

(54) FLUORO-CONTAINING DERIVATIVES OF HYDROGENATED PYRIDO[4,3-B]INDOLES WITH NEUROPROTECTIVE AND COGNITION ENHANCING PROPERTIES, PROCESS FOR PREPARING, AND USE

(75) Inventors: Alexey Aksinenko, Chernogolovka (RU); Sergey Bachurin, Chernogolovka (RU); Sergey Sablin, San Francisco, CA (US); Bogdan Beznosko, Chernogolovka (RU); Nadezhda Beznosko, legal representative, Chernogolovka (RU); Julia Beznosko, legal representative, Chernogolovka (RU); Vladimir Sokolov, Chernogolovka (RU)

(73) Assignee: D2E, LLC, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/621,464

(22) Filed: Nov. 18, 2009

(65) Prior Publication Data

US 2010/0056790 A1   Mar. 4, 2010

Related U.S. Application Data

(63) Continuation of application No. 12/284,291, filed on Sep. 19, 2008.

(60) Provisional application No. 60/994,903, filed on Sep. 20, 2007.

(51) Int. Cl.
*C07D 471/04* (2006.01)
*A61K 31/437* (2006.01)
(52) U.S. Cl. ......................................... 546/82; 514/290
(58) Field of Classification Search .................... 546/82; 514/290
See application file for complete search history.

(56) References Cited

U.S. PATENT DOCUMENTS

| 3,409,628 | A | 11/1968 | Berger et al. |
| 3,484,449 | A | 12/1969 | Berger et al. |
| 3,502,688 | A | 3/1970 | Berger et al. |
| 3,522,262 | A | 7/1970 | Berger et al. |
| 3,646,045 | A | 2/1972 | Berger et al. |
| 3,654,290 | A | 4/1972 | Berger et al. |
| 6,133,282 | A | 10/2000 | Horvath et al. |
| 6,187,785 | B1 | 2/2001 | Zefirov et al. |
| 6,350,757 | B1 | 2/2002 | Goldstein et al. |
| 6,469,021 | B1 | 10/2002 | Truesdale et al. |
| 6,506,768 | B2 | 1/2003 | Kennis et al. |
| 7,071,206 | B2 | 7/2006 | Zefirov et al. |
| 7,109,339 | B2 | 9/2006 | Lee et al. |
| 7,115,621 | B2 | 10/2006 | Sawyer et al. |
| 2001/0020028 | A1 | 9/2001 | Zefirov et al. |
| 2002/0115682 | A1 | 8/2002 | Zefirov et al. |
| 2004/0044022 | A1 | 3/2004 | Zefirov, Jr. et al. |
| 2005/0031651 | A1 | 2/2005 | Gervais et al. |
| 2005/0143371 | A1 | 6/2005 | Meyers et al. |
| 2006/0140866 | A1 | 6/2006 | Zefirov et al. |
| 2006/0167259 | A1 | 7/2006 | Chao et al. |
| 2007/0027178 | A1 | 2/2007 | Lee |
| 2007/0117834 | A1 | 5/2007 | Hung |
| 2007/0117835 | A1 | 5/2007 | Hung |
| 2007/0179174 | A1 | 8/2007 | Bachurin et al. |
| 2007/0225316 | A1 | 9/2007 | Bachurin et al. |
| 2008/0234310 | A1 | 9/2008 | Bachurin et al. |
| 2008/0280942 | A1 | 11/2008 | Diaz-Fernandez et al. |
| 2009/0221627 | A1 | 9/2009 | Aksinenko et al. |
| 2009/0227619 | A1 | 9/2009 | Wu et al. |

FOREIGN PATENT DOCUMENTS

| EP | 0017727 A | 10/1980 |
| SU | 1138164 A | 2/1985 |
| WO | WO2006040451 A2 | 4/2006 |
| WO | WO2006101434 A1 | 9/2006 |
| WO | WO2006125887 A1 | 11/2006 |
| WO | WO2007041697 A3 | 4/2007 |
| WO | WO2008036400 A2 | 3/2008 |
| WO | WO2008036410 A2 | 3/2008 |
| WO | WO2008051599 A3 | 5/2008 |
| WO | WO2008069963 A1 | 6/2008 |
| WO | WO2008073231 A1 | 6/2008 |
| WO | WO2009005771 A1 | 1/2009 |
| WO | WO2009017836 A1 | 2/2009 |
| WO | WO2009039420 A1 | 3/2009 |

OTHER PUBLICATIONS

Flourinated Pharmaceuticals, 2003, Dr. Wakefeild.*
Dimenbon, Lermantova et al, 2000.*
Samuel Samnick et al, 1996. Synthesis and Preliminary In vitro evaluation of a new Memantine derivative 1-amino-3 fluoromethyl-5-methyl-adamantane.*
Kost et al., Addition of Aromatic Amines and Phenylhydrazine to 2-methyl-5-vinylpyridine, Zhurnal Obshchei Khimii (1960), 30, 2556-62. Accession No. 1961:70664 CAPLUS.
Trofimov et al., "Pyridylethylation of Gamma-Carbolines," Khimiko-Farmatsevticheskii Zhurnal (1967), 1(3), 22-5. Accession No. 1967:500029 CAPLUS.

(Continued)

*Primary Examiner* — Rita J Desai
(74) *Attorney, Agent, or Firm* — Carr & Farrell LLP

(57) ABSTRACT

Some exemplary embodiments comprise fluoro-containing derivatives of pyrido[4,3-b]indoles (and exemplary methods of making the same) that may be administered to a mammal (including a human) in an effective amount for potential use in the treatment or prophylaxis of neurological disorders including AD, mild cognitive impairment, senile and vascular dementia, HD, ALS, Parkinson's disease, AIDS-related dementia, ischaemic cerebral pathologies, neuropathic pain, ADHD (attention deficit disorder/hyperactivity syndrome), eating disorders such as anorexia and bulimia, panic attacks, withdrawal from drug abuse such as cocaine, ethanol, nicotine and benzodiazepines, schizophrenia (in particular the cognitive deficit of schizophrenia), stroke and also disorders associated with spinal trauma and/or head injury. These derivatives may also be useful for the treatment of borderline personality disorder, obesity, and for use as geroprotectors. The compounds may also be used as "pharmacological tools" for an investigation of the mechanism of protection against neurodegeneration disorders in vivo or in vitro.

2 Claims, 7 Drawing Sheets

OTHER PUBLICATIONS

Kost et al., "Reactions of Hydrazine Derivatives. XXXIX. Addition of Hydrazine and Substituted Hydrazines to 2-vinylpyridine," Zhurnal Obschei Khimii (1963), 33 (11), 3606-13. Accession No. 1694:45681 CAPLUS.

De Silva et al., "Spectrofluorometric Determination of Substituted Tetrahydrocabazoles by a Methylene Blue Sensitized Photolytic Reaction," Journal of Pharmaceutical Sciences (1977), 66(3), 353-7. Accession No. 1977:1641979 CAPLUS.

Strojny et al., "Luminescence Analysis of Anti-Inflammatory Agents in Blood or Plasma Following Thin-Layer Chromatographic Separation," Journal of Chromatographic Science (1975), 13(12), 583-8. Accession No. 1976:99035 CAPLUS.

Jenny et al., "Nucleophilic Displacement Reactions of Some Halogen-Substituted Phenylcyclobutenes and the Ring-Opening Reaction of 2-chloro-4-piperidino-3-phenyl-2-cyclobutenone," Journal of the American Chemical Society (1960), 82, 3111-17. Accession No. 1961:70663 CAPLUS.

Lermontova, et al. "Dimebon Improves Learning in Animals with Experimental Alzheimer's Disease," Bulletin of Experimental Biology and Medicine (2000), 129(6).

Wakefield, et al. "Fluorinated Pharmaceuticals," Innovations in Pharmaceutical Technology, 2003.

Samnick et al, "Synthesis and Preliminary In Vitro Evaluation of a new Memantine Derivative 1-amino-3-fluoromethyl-5-methyl-adamantane," Journal of Labelled Compounds and Radiopharmaceuticals (1996), 39(3).

The Stille Reaction, Myers et al., 1998.

Organic Synthesis, Stille Reaction, 1995 Hassner et al.

Tamiz et al., "Structure- Activity Relationship for a Series of 2-Substituted 1,2,3,4-tetrahydro-9H-pyrido [3,4-b]indoles: Potent Subtype-Selective Inhibitors of (NMDA) Receptors," Bioorganic & Medicinal Chemistry Letters, vol. 9, Issue 11, Jun. 7, 1999, pp. 1619-1624.

Bringmann et al., "1-Trichloromethy1-1,2,3,4-tetrahydro-β-carboline (TaClo) and Related Derivatives: Chemistry and Biochemical Effects on Catecholamine Biosythesis," Bioorganic & Medicinal Chemistry, vol. 10, Issue 7, Jul. 2002, pp. 2207-2214.

Nagai et al., "Synthesis of 2 3 4 4a 5 9b Hexa Hyrdo-1h Pyrido-4-3-B Indole Derivatives and Their Central Nervous System Activities," Journal of Medicinal Chemistry (1979),226(6), 677-683. Accession No. 1980:136861 BIOSIS.

Welch et al., "Neuroleptics From the 4a 9b-Trans-2 3 4 4a 5 9b Hexahydro-1h-Pyrido-4 3-B-Indole Series 3. Carboxamidoalkyl Derivatives." Accession No. 1987:7292 BIOSIS.

Gill et al., "Identification of Novel p38 MAP Kinase Inhibitors Using Fragment-Based Lead Generation," Journal of Medical Chemistry (2005), 48 (2), 414-426.

Organic Chemistry, fifth edition, 2009, William Brown, pp. 799-801.

* cited by examiner

| Structure | Yield, NMR, % (Reaction mixture) | Isolated yield, base % | Melting point for HCl salts, °C |
|---|---|---|---|
|  (1) | 62 | 37 | 235-237 |
|  (2) | 41 | 11 | 238-240 |
|  (3) | 76 | 40 | 237-239 |
|  (4) | 63 | 47 | 252-254 |
|  (5) | 74 | 27 | 213-215 |
|  (6) | 46 | 30 | 214-216 |

| Structure | | | |
|---|---|---|---|
| (7) | 9 | | |
| (8) | 74 | 26 | 250-252 |
| (9) | 67 | | |
| (10) | 57 | 20 | 228-230 |
| (11) | 66 | 36 | 220-222 |
| (12) | 42 | 30 | 216-218 |
| (13) | 59 | | |
| (14) | 23 | 19 | 92-93 |
| (15) | | 36 | 241-243 |

FIG. 1B

| ID | R1 | R2, R3 | CH2(1) | CH2(3) | CH2(4) | H6 | H7 | H8 | H9 | H2 | H4 | H6 | CH2 | CH2Py | 19F |
|---|---|---|---|---|---|---|---|---|---|---|---|---|---|---|---|
| | R1 | | | | | | | | | | | | CH2CH2Py | | |
| | H+ | | | | | | | | | | | | | | |
| 1 | 2.95 d 3H, J 4.9 | 11.23 broad s | 4.29 m 1H, 4.62 m 1H | 3.05-3.24 m 4H | | 7.09 m 2H, 7.46 m 2H | | | | 8.53 d J 3 | 7.80 d J(HF) 9 | 8.33 s | 4.45 t 2H | 3.46 m 1H, 3.76 m 1H | -48.70 d J(HF) 9 |
| 2 | 2.92 d 3H, J 4.4 | 11.39 broad s 2.36 s 3H | 4.24 m 1H, 4.55 m 1H | 3.07-3.26 m 4H | | 7.34 d J 8.6 | 6.95 d J(HH) 8.6 | | 7.21 s | 8.58 br. s | 7.88 d J(HF) 9.7 | 8.36 s | 4.38 t 2H | 3.43 m 1H, 3.70 m 1H | -47.23 d J(HF) 9 |
| 3 | 2.95 d 3H, J 4.9 | 11.23 broad s | 4.23 m 1H, 4.54 m 1H | 3.07-3.24 m 4H | | 7.47 dd J(HH) 9.1 J(HF) 4.2 | 6.96 ddd J(HH) 2.7, 9.1 J(HF) 9.7 | | 7.27 dd J(HH) 2.7 J(HF) 9.7 | 8.51 d J 3 | 7.78 d J(HF) 9 | 8.30 s | 4.43 t 2H | 3.46 m 1H, 3.76 m 1H | -46.51 dt J 4.2, J 9.7<br>-49.00 d 1F J(HF) 9 |

FIG. 2A

| | | | | | | | | | | | |
|---|---|---|---|---|---|---|---|---|---|---|---|
| 4 | 2.92 d 3H, J 4.4 | 11.51 broad s | | 4.24 m 1H, 4.55 m 1H | 3.07-3.26 m 4H | 7.48 d J 8.8 | 7.10 dd J(HH) 2.3, 8.8 | | 7.55 d J 2.3 | 8.58 d J 3 | 7.89 d J(HF) 9.7 | 8.37 s | 4.43 t 2H | 3.44 m 1H, 3.75 m 1H | -47.98 d J(HF) 9.7 |
| 5 | 2.92 d 3H, J 4.4 | 11.39 broad s | | 4.24 m 1H, 4.58 m 1H | 3.07-3.26 m 4H | 7.44 d J 8.6 | 7.22 d J 8.6 | | 7.69 s | 8.48 d J 3 | 7.76 d J(HF) 9.5 | 8.28 s | 4.43 t 2H | 3.44 m 1H, 3.72 m 1H | -49.21 d J(HF) 9.5 |
| 6 | 2.94 d 3H, J 4.4 | 10.96 broad s | 3.77 s 3H | 4.24 m 1H, 4.55 m 1H | 3.07-3.26 m 4H | 7.36 d J 8.6 | 7.10 dd J(HH) 2.3, 8.6 | | 6.98 d J 2.3 | 8.48 d J 3 | 7.72 d J(HF) 9.7 | 8.29 s | 4.37 t 2H | 3.42 m 1H, 3.73 m 1H | -49.36 d J(HF) 9 |
| 7 | 2.63 s 3H | | 2.35 s 3H, 2.42 s 3H | 3.48 s 2H | 2.20 -2.85 m 4H | 6.58 s | | 6.91 s | 8.26 d J 3 | 6.66 d J(HF) 9.7 | 8.09 s | 4.34 t J(HH) 6 | 2.89 t J(HH) 6 | 2.63 s 3H | |
| 8 | 2.93 d 3H, J 4.9 | 11.25 broad s | | 4.23 m 1H, 4.55 m 1H | 3.07-3.24 m 4H | | 6.98 ddd J(HH) 2.0, J(HF) 9.0, 9.7 | | 7.18 dd J(HH) 2.0 J(HF) 9.7 | 6.43 d J 3 | 7.54 d J(HF) 9.8 | 8.14 s | 4.47 m 2H | 3.46 m 1H, 3.76 m 1H | -44.48 d 1F J 3<br>-49.91 s 1F<br>-53.25 d 1F J 3 |
| 9 | | | 2.38 s 3H | 3.71 s 2H | 2.55 m 2H; 2.78 m 2H | 7.27 d J(HH) 8.8 | | 7.75 s | 8.38 d J(HH) 3 | 6.91 dt J(HF) 9, J(HH) 3 | 8.17 s | 4.33 t 2H, J 7.0 | 3.09 t 2H, J 7.0 | | |
| 10 | 2.95 d 3H, J 4.0 | 11.43 broad s | | 4.23 m 1H, 4.54 m 1H | 3.07-3.24 m 4H | 7.56 d J(HH) 9.3 | 7.07 dd J(HH) 1.7, 9.3 | | 7.49 s | 8.53 d J 2 | 7.82 d J(HF) 9.7 | 8.36 s | 4.43 m 2H | 3.46 m 1H, 3.76 m 1H | 20.81 s 3F<br>-48.63 d 1F J(HF) 8.5 |

| | | | | | | | | | | | | |
|---|---|---|---|---|---|---|---|---|---|---|---|---|
| 11 | 1.40 t 3H, 3.29 m 2H | 11.00 broad s | | 4.29 m 1H, 4.63 m 1H | 3.05-3.24 m 4H | 7.07 m 2H, 7.47 m 2H | | 8.48 d J 3 | 7.76 d J(HF) 9 | 8.30 s | 4.25 m 2H | 3.46 m 1H, 3.76 m 1H | -49.07 d J(HF) 9 |
| 12 | 1.38 t 3H, 3.27 m 2H | 10.87 broad s | 2.38 s 3H | 4.30 m 1H, 4.58 m 1H | 3.06-3.25 m 4H | 7.34 d J(HH) 8.0 | 7.27 s | 8.49 d J 3 | 7.75 d J(HF) 9 | 8.27 s | 4.26 m 2H | 3.45 m 1H, 3.78 m 1H | -49.13 d J(HF) 9 |
| 13 | 3.57 s 2H | 7.09-7.37 m 5H | 2.38 s 3H | 3.66 s 2H | 2.24 t 2H J(HH) 5.6; 2.65 t 2H J(HH) 5.6 | 6.95 d J(HH) 8.0 | 7.06 s | 8.25 d J 3 | | 8.04 s | 4.12 t J(HH) 6.7 | 2.50 t J(HH) 6.7 | 3.57 s 2H |
| 14 CDCL3 | 1.24 t 3H, 2.68 k 2H | 11.23 broad s | | 3.67 s 2H | 2.55 m 2H | 6.83 d J(HH) 8.0 | | 8.38 d J 3 | 7.12 m | 8.16 s | 426 t 2H | 3.06 t 2H | -47.37 dt J 4.4, J 9.7 |
| | | | | | 2.80 m 2H | 6.91 m 2H | | | | | | | -49.10 d 1F J(HF) 9 |
| 15 | 1.37 t 3H, 3.08 m 2H | 10.56 broad s | | 4.24 m 1H, 4.65 m 1H | 3.07-3.30 m 4H | 7.46 d J 8.0 | 7.0 d J(HH) 8.0 | 8.70 br. s | 8.09 d J(HF) 9 | 8.45 s | 4.45 m 2H | 3.44 m 1H, 3.80 m 1H | -48.93 d J(HF) 9 |
|  | | | | | | | 7.59 s | | | | | | |

Influence of compound 5 on object exploration in familiar and new localizations.
FL – familiar localization of familiar object; NL - new localization of familiar object.

Influence of compound 8 on object exploration in familiar and new localizations. FL – familiar localization of familiar object; NL - new localization of familiar object.

FLUORO-CONTAINING DERIVATIVES OF HYDROGENATED PYRIDO[4,3-B]INDOLES WITH NEUROPROTECTIVE AND COGNITION ENHANCING PROPERTIES, PROCESS FOR PREPARING, AND USE

CROSS-REFERENCE TO RELATED APPLICATION

This continuation application claims the benefit and priority of U.S. Non-Provisional patent application Ser. No. 12/284,291 filed on Sep. 19, 2008, titled "Fluoro-Containing Derivatives of Hydrogenated Pyrido[4,3-b]indoles with Neuroprotective and Cognition Enhancing Properties, Process for Preparing, and Use," which in turn claims the benefit and priority of U.S. Provisional Patent Application Ser. No. 60/994,903 filed on Sep. 20, 2007, titled "Novel Fluoro-containing Derivatives of Hydrogenated Pyrido[4,3-b]indoles with Neuroprotective and Cognition Enhancing Properties, Process for Preparing Them and Their Use," all of which are hereby incorporated by reference.

BACKGROUND OF THE INVENTION

1. Field of the Invention

This invention relates to chemical compounds in medicine, and more specifically to fluoro-containing derivatives of hydrogenated pyrido[4,3-b]indoles with neuroprotective and cognition enhancing properties, process for preparing and use.

2. Description of Related Art

Under normal physiological conditions, excitatory amino acids ("EEAs") are involved in the neural pathways associated with learning and memory [Wang H., Hu Y., Tsein J. Z. Molecular and systems mechanisms of memory consolidation and storage. Prog. Neurobiol. 2006; 79(3):123-35]. A variety of neurological disorders and neurodegenerative diseases, such as Alzheimer's disease ("AD"), Huntington's disease ("HD"), amyotrophic lateral sclerosis ("ALS") and brain ischemia are associated with an excitotoxic effect of endogenous neuromediatory excitatory amino acids, such as glutamic and aspartic acids [a) Stemmer J. E., De Zeeuw C. I., Weber J. T. Don't get too excited: mechanisms of glutamate-mediated Purkinje cell death. Prog. Brain Res. 2005; 148: 367-90; b) Doble A. The role of excitotoxicity in neurodegenerative disease: implications for therapy. Pharmacol Ther. 1999; 81(3):163-221]. In accordance with this mechanism, hyperexcitation of neurons (i.e. prolonged activation of their NMDA, AMPA/kainate receptors with EAA) results in excessive entry of calcium ions into the neuronal cells [Kwak S., Weiss J. H. Calcium-permeable AMPA channels in neurodegenerative disease and ischemia. Curr. Opin. Neurobiol. 2006; 16(3):281-7]. Calcium influx into an NMDA channel takes place following an action potential when a glutamatergic presynaptic neuron releases glutamate molecules into a synapse. The released glutamate interacts with the catalytic site of the NMDA receptor on the post-synaptic neuron and, once the channel is freed of magnesium that occupies it under rest conditions, allows calcium influx from the extracellular medium into the intracellular medium. If the NMDA channel remains open to the calcium influx for more than a few milliseconds (pathological conditions), a cascade of intracellular reactions is initiated, leading to neuronal death (apoptosis).

Accordingly, the NMDA receptor is an attractive and validated target for the treatment of AD [Samanta M. K., Wilson B., Santhi K., Suresh B. Alzheimer disease and its management: a review. Am. J. Ther. 2006 November-December; 13(6):516-26]. Therapeutic intervention may take place either by blocking the influx of calcium ions ("corking-up" the channel) [Albensi B. C., Ilkanich E. Open-channel blockers of the NMDA receptor complex. Drug News Perspect. 2004; 17(9):557-62] or by interaction with the NMDA receptor binding site. Research indicates that NMDA receptor antagonists have the potential to prevent injury and death of neurons related to a variety of conditions [Gerber A. M., Vaallano M. L. Structural properties of the NMDA receptor and the design of neuroprotective therapies. Mini Rev. Med. Chem. 2006; 6(7):805-15], including ischaemic cerebral pathologies, neuropathic pain, ALS, AD [Wenk G. L. Neuropathologic changes in Alzheimer's disease: potential targets for treatment. J. Clin. Psychiatry 2006; 67 Suppl. 3:3-7; quiz 23], HD, and AIDS-related dementia.

SUMMARY OF THE INVENTION

Some exemplary embodiments comprise fluoro-containing derivatives of pyrido[4,3-b]indoles (and exemplary methods of making the same) that may be represented by the general chemical formula I (below) or its optical antipodes, racemates, or pharmaceutically acceptable salts and/or solvates thereof,

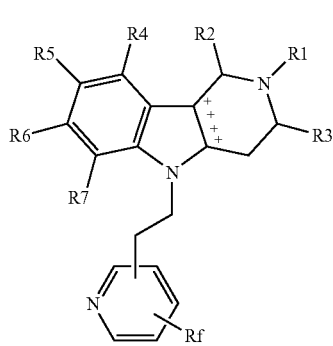

I wherein:
the solid line accompanied by the dotted line (═) represents a single or double bond;
$R^f$ is chosen from a fluorine atom, two fluorine atoms, or a trifluoromethyl group;
$R^1$ is chosen from a H, $(C_1-C_6)$alkyl; hydroxy$(C_2-C_6)$alkyl; (hetero)aryl$(C_2-C_6)$alkyl; $(C_3-C_7)$cycloalkyl; $(C_2-C_6)$alkenyl; $(C_1-C_6)$alkylsulfonyl; (hetero)arylsulfonyl; $(C_1-C_6)$alkanoyl; (hetero)aroyl, $(C_1-C_6)$alkoxycarbonyl; $(C_1-C_6)$alkoxy$(C_1-C_6)$alkyl; (hetero)aryloxy$(C_1-C_6)$alkyl; amino$(C_1-C_6)$alkyl, wherein the amino group may be optionally substituted by alkyl, (hetero)aryl, alkenyl, alkanoyl, (hetero)aroyl and other; or a group $CONR^8R^9$ or $SO_2NR^8N^9$, wherein $R^8$ and $R^9$ independently represent hydrogen or $(C_1-C_6)$alkyl, or $R^8$ and $R^9$ together with the nitrogen atom to which they are attached may form a nitrogen-containing heterocyclic or nitrogen-containing heteroaryl group;
$R^2$ and $R^3$ are chosen independently from a hydrogen and a methyl group; $R^2$ and $R^3$ together may form a chain of formula —$CH_2CH_2$—; and
$R^4$, $R^5$, $R^6$ and $R^7$ each represent, independently of each other, a hydrogen or halogen atom or a trifluoromethyl, trifluoromethoxy, cyano, hydroxyl, $(C_1-C_6)$ alkyl, $(C_1-C_6)$ alkoxy, phenoxy, phenyl or pyridyl group optionally substituted with a halogen atom or a methyl, methoxy, cyano, trifluoromethyl, or hydroxyl group.

Some embodiments comprise administering to a mammal (including a human) an effective amount of a pyrido[4,3-b]indole derivative. These derivatives are believed to be of potential use in the treatment or prophylaxis of neurological disorders including AD, mild cognitive impairment, senile and vascular dementia, HD, ALS, Parkinson's disease, AIDS-related dementia, ischaemic cerebral pathologies, neuropathic pain, ADHD (attention deficit disorder/hyperactivity syndrome), eating disorders such as anorexia and bulimia, panic attacks, withdrawal from drug abuse such as cocaine, ethanol, nicotine and benzodiazepines, schizophrenia (in particular the cognitive deficit of schizophrenia), stroke and also disorders associated with spinal trauma and/or head injury. These derivatives may also be useful for the treatment of borderline personality disorder, obesity, and for use as geroprotectors, which may be applied for slowing aging, prolonging lifespan of an individual or cells in an individual, and/or improving quality of life of an individual developing or having a risk of developing age-associated manifestations and/or pathologies.

BRIEF DESCRIPTION OF THE DRAWINGS

FIGS. 1A-1B is a table of yields and melting points for various exemplary compounds presented herein;

FIGS. 2A-2C is a table of NMR data for various exemplary compounds presented herein;

DETAILED DESCRIPTION OF THE INVENTION

Figure 1A:
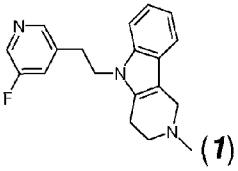
Figure 1A:
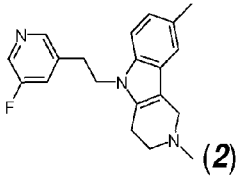
Figure 1A:
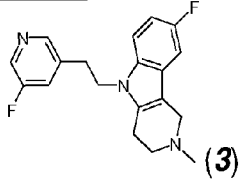
Figure 1A:
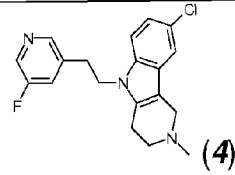
Figure 1A:
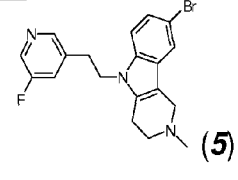
Figure 1A:
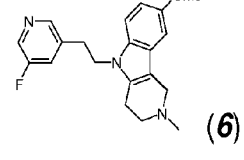

Exemplary embodiments presented herein include novel fluoro-containing pyridoethyl derivatives of pyrido[4,3-b]indoles for modulation of calcium cellular pathways (e.g., as blockers of glutamate-induced transport of calcium ions), for antagonism of specific serotonin receptors (e.g., 5-HT6), for efficient neuroprotection, for use as cognition-enhancing agents, for treatment of neurological disorders and neurodegenerative diseases (e.g., Alzheimer's disease), for research, drug screening, and therapeutic applications. Also provided herein are exemplary methods of making such fluoro-containing pyridoethyl derivatives of pyrido[4,3-b]indoles.

First generation NMDA antagonist clinical trial results were largely disappointing, often owing to CNS side effects. NMDA antagonists with improved tolerability have now been identified, such as memantine and dimebon.

The aminoadamantane derivative memantine is a non-competitive and a low to moderate affinity NMDA antagonist (blocker of an open NMDA channel), and seems to lack the CNS side effects. This drug is approved for treatment of moderate to severe dementia of the AD type [Cosman K. M., Boyle L. L., Porsteinsson A. P. Memantine in the treatment of mild-to-moderate Alzheimer's disease. Expert Opin. Pharmacother. 2007; 8(2):203-14].

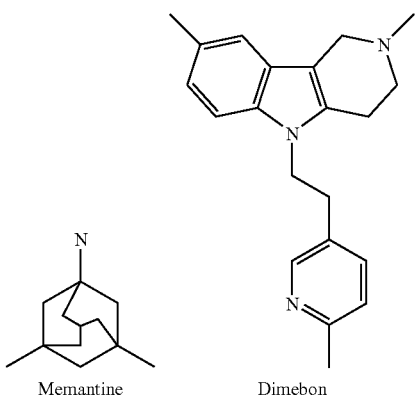

Memantine                Dimebon

The gamma-carboline derivative dimebon is a non-competitive NMDA antagonist that does not interact with calcium channels [Grigoriev V., Dranyi O., Bachurin S., Comparative study of action mechanisms of dimebon and memantine on AMPA- and NMDA-subtypes glutamate receptors in rat cerebral neurons. Bull. Exp. Biol. Med. 2003; 136(5): 474-7], and effectively blocks the glutamate-induced transport of calcium ions into neurons. Dimebon displays expressed neuroprotective and cognition-enhancing properties in animal models of dementia as well in human clinical trials [Bachurin S., Bukatina E., Lermontova N., Tkachenko S., Afanasiev A., Grigoriev V., Grigorieva I., Sablin S., Zefirov N. Antihistamine agent Dimebon as a novel neuroprotector and a cognition enhancer. Ann. N.Y. Acad. Sci. 2001; 939: 425-35].

In a one-year, randomized, double-blinded, placebo-controlled trial of 183 patients with mild to moderate AD, dimebon met all five clinical endpoints with strong statistical significance, and was very well tolerated [Doody R. S., Gavrilova S. I., Sano M., Thomas R. G., Aisen P. S., Bachurin S. O., Seely L., Hung D. Effect of dimebon on cognition, activities of daily living, behaviour, and global function in patients with mild-to-moderate Alzheimer's disease: a randomised, double-blind, placebo-controlled study. Lancet 2008; 372: 207-15]. This medicine is now in the final step of clinical trials for AD, and is entering into Phase II of clinical trails for HD.

There has been increasing interest in the role of serotonin receptors regarding memory formation and retrieval [Foley A. G., Murphy K. J., Hirst W. D., Gallagher H. C., Hagan J. J., Upton N., Walsh, F. S., Regan, C. M. The 5-HT(6) receptor antagonist SB-271046 reverses scopolamine-disrupted consolidation of a passive avoidance task and ameliorates spatial task deficits in aged rats. Neuropsychopharmacology 2004; 29: 93-100]. Fourteen serotonin receptors have been identified thus far, each coupled to one of four different signaling complexes. The 5-HT6 receptor, which stimulates cAMP production through adenylate cyclase and Gs-protein activation, is one of the most recently discovered [Monsma F. J., Shen Y., Ward R. P., Hamblin M. W., Sibley D. R., 1993. Cloning and expression of a novel serotonin receptor with high affinity for tricyclic psychotropic drugs. Molecular Pharmacology 43, 320-327]. Immunohistochemical detection of 5-HT6 receptors using electron microscopy indicates that expression is almost exclusively within the neurophil, with very little expression in neuronal soma [Hamon M., Doucet E., Lefevre K., Miguel M. C., Lanfumey L., Insausti R., Frechilla D., Del Rio J., Verge D. Antibodies and antisense oligonucleotide for probing the distribution and putative functions of central 5-HT6 receptors. Neuropsychopharm.

1999; 21: 68-76]. In addition to widespread expression within the brain, 5-HT6 receptors appear to modulate many neurotransmitter systems, including glutamatergic, dopaminergic, noradrenergic and cholinergic signaling [Lacroix L. P., Dawson L. A., Hagan J. J., Heidbreder C. A. 5-HT6 receptor antagonist SB-271046 enhances extracellular levels of monoamines in the rat medial prefrontal cortex. Synapse 2004; 51: 158-164]. Accordingly, 5-HT6 receptors have been implicated as possible drug targets for several neuropsychiatric disorders known to be influenced by these neurotransmitter systems, such as schizophrenia, depression and some types of dementia [Woolley M. L., Marsden C. A., Fone K. C. 5-ht6 Receptors. Current Drug Targets. CNS and Neurological Disorders 2004; 3: 59-79].

| Drug ID | Highest Phase | Organization | Therapeutic Group |
| --- | --- | --- | --- |
| BGC-20-761 | Preclinical | BTG (London) | Antipsychotic Drugs Treatment of Cognition Disorders |
| SGS-518 | Phase II | Lilly, Saegis | Treatment of Cognition Disorders |
| SB-742457 | Phase II | GlaxoSmithKline | Treatment of Alzheimer's Dementia, Antipsychotic Drugs |
| FMPD | Preclinical | Lilly | Antipsychotic Drugs |
| PRX-07034 | Phase I | Epix Pharm. | Antiobesity Drugs Antipsychotic Drugs Treatment of Cognition Disorders |
| SB-737050A | Phase II | GlaxoSmithKline | Antipsychotic Drugs |
| BVT-74316 | Phase I | Biovitrum | Antiobesity Drugs |
| SAM-315 | Phase I | Wyeth Pharm. | Treatment of Alzheimer's Dementia |
| SYN-114 | Phase I | Roche Synosis Ther. | Treatment of Cognition Disorders |

There are several 5-HT6 antagonists under active development at the highest phases of clinical trials, but no information has been found regarding compounds with combined NMDA, 5-HT6 antagonist, and/or BuChE inhibitor properties.

Compounds

Some exemplary embodiments comprise fluoro-containing derivatives of pyrido[4,3-b]indoles that may be represented by the general chemical formula I (below) or its optical antipodes, racemates, or pharmaceutically acceptable salts and/or solvates thereof,

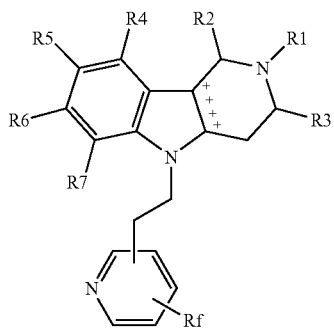

I wherein:
the solid line accompanied by the dotted line (⸺) represents a single or double bond;
$R^f$ is chosen from a fluorine atom, two fluorine atoms, or a trifluoromethyl group;
$R^1$ is chosen from a H, $(C_1-C_6)$alkyl; hydroxy$(C_2-C_6)$alkyl; (hetero)aryl$(C_2-C_6)$alkyl; $(C_3-C_7)$cycloalkyl; $(C_2-C_6)$alkenyl; $(C_1-C_6)$alkylsulfonyl; (hetero)arylsulfonyl; $(C_1-C_6)$alkanoyl; (hetero)aroyl, $(C_1-C_6)$alkoxycarbonyl; $(C_1-C_6)$alkoxy$(C_1-C_6)$alkyl; (hetero)aryloxy$(C_1-C_6)$alkyl; amino $(C_1-C_6)$alkyl, wherein the amino group may be optionally substituted by alkyl, (hetero)aryl, alkenyl, alkanoyl, (hetero)aroyl and other; or a group $CONR^8R^9$ or $SO_2NR^8N^9$, wherein $R^8$ and $R^9$ independently represent hydrogen or $(C_1-C_6)$alkyl, or $R^8$ and $R^9$ together with the nitrogen atom to which they are attached may form a nitrogen-containing heterocyclic or nitrogen-containing heteroaryl group;
$R^2$ and $R^3$ are chosen independently from a hydrogen and a methyl group; $R^2$ and $R^3$ together may form a chain of formula —$CH_2CH_2$—;
$R^4$, $R^5$, $R^6$ and $R^7$ each represent, independently of each other, a hydrogen or halogen atom or a trifluoromethyl, trifluoromethoxy, cyano, hydroxyl, $(C_1-C_6)$ alkyl, $(C_1-C_6)$ alkoxy, phenoxy, phenyl or pyridyl group optionally substituted with a halogen atom or a methyl, methoxy, cyano, trifluoromethyl, or hydroxyl group;
$R^5$ and $R^6$ together may form a cyclic group of formula —$OCH_2O$—, —$OCH_2CH_2O$— or —$CH_2CH_2CH_2CH_2$—;
Some embodiments comprise the use of the compound of formula I, wherein:
$R^f$ is chosen from a fluorine atom or a trifluoromethyl group;
$R^1$ is chosen from a H, $(C_1-C_6)$alkyl; hydroxy$(C_2-C_6)$alkyl; (hetero)aryl$(C_2-C_6)$alkyl; $(C_3-C_7)$cycloalkyl; or $(C_2-C_6)$alkenyl;
$R^2$ and $R^3$ are chosen independently from a hydrogen and a methyl group; $R^2$ and $R^3$ together may form a chain of formula —$CH_2CH_2$—;
$R^4$, $R^5$, $R^6$ and $R^7$ each represent, independently of each other, a hydrogen or halogen atom or a trifluoromethyl, trifluoromethoxy, cyano, hydroxyl, methyl, ethyl, methoxy, ethoxy, cyano, or hydroxyl group;
$R^5$ and $R^6$ together may form a cyclic group of formula —$OCH_2O$—;
Some embodiments may comprise the use of the compound of formula Ia (below),

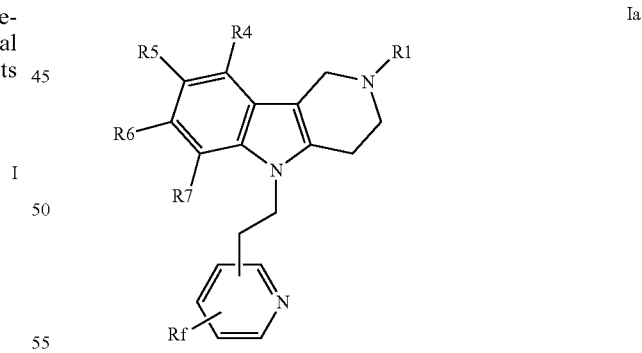

Ia wherein:
$R^f$ is chosen from a fluorine atom or a trifluoromethyl group;
$R^1$ is chosen from a H, methyl, ethyl, cyclopropyl, 2-hydroxyethyl, benzyl, or phenethyl, wherein the last two (i.e. the benzyl, or phenethyl) may be optionally substituted by halogen atoms and methyl or methoxy groups;
$R^4$, $R^5$, $R^6$ and $R^7$ each represent, independently of each other, a hydrogen or halogen atom or a trifluoromethyl, trifluoromethoxy, cyano, hydroxyl, methyl, ethyl, methoxy, ethoxy, cyano, or group.

In some embodiments, the compound is either:
5-[2-(5-fluoropyridin-3-yl)ethyl]-2-methyl-2,3,4,5-tetrahydro-1H-pyrido[4,3-b]indole;
5-[2-(5-fluoropyridin-3-yl)ethyl]-2,8-dimethyl-2,3,4,5-tetrahydro-1H-pyrido[4,3-b]indole;
8-fluoro-5-[2-(5-fluoropyridin-3-yl)ethyl]-2-methyl-2,3,4,5-tetrahydro-1H-pyrido[4,3-b]indole;
8-chloro-5-[2-(5-fluoropyridin-3-yl)ethyl]-2-methyl-2,3,4,5-tetrahydro-1H-pyrido[4,3-b]indole;
8-bromo-5-[2-(5-fluoropyridin-3-yl)ethyl]-2-methyl-2,3,4,5-tetrahydro-1H-pyrido[4,3-b]indole;
5-[2-(5-fluoropyridin-3-yl)ethyl]-8-methoxy-2-methyl-2,3,4,5-tetrahydro-1H-pyrido[4,3-b]indole;
5-[2-(5-fluoropyridin-3-yl)ethyl]-2,6,8-trimethyl-2,3,4,5-tetrahydro-1H-pyrido[4,3-b]indole;
6,8-difluoro-5-[2-(5-fluoropyridin-3-yl)ethyl]-2-methyl-2,3,4,5-tetrahydro-1H-pyrido[4,3-b]indole;
5-[2-(5-fluoropyridin-3-yl)ethyl]-2-methyl-8-(trifluoromethyl)-2,3,4,5-tetrahydro-1H-pyrido[4,3-b]indole;
5-[2-(5-fluoropyridin-3-yl)ethyl]-2-methyl-8-(trifluoromethoxy)-2,3,4,5-tetrahydro-1H-pyrido[4,3-b]indole;
2-ethyl-5-[2-(5-fluoropyridin-3-yl)ethyl]-2,3,4,5-tetrahydro-1H-pyrido[4,3-b]indole;
2-ethyl-5-[2-(5-fluoropyridin-3-yl)ethyl]-8-methyl-2,3,4,5-tetrahydro-1H-pyrido[4,3-b]indole;
2-benzyl-5-[2-(5-fluoropyridin-3-yl)ethyl]-8-methyl-2,3,4,5-tetrahydro-1H-pyrido[4,3-b]indole;
2-ethyl-8-fluoro-5-[2-(5-fluoropyridin-3-yl)ethyl]-2,3,4,5-tetrahydro-1H-pyrido[4,3-b]indole;
8-chloro-2-ethyl-5-[2-(5-fluoropyridin-3-yl)ethyl]-2,3,4,5-tetrahydro-1H-pyrido[4,3-b]indole;
2-methyl-5-{2-[6-(trifluoromethyl)pyridin-3-yl]ethyl}-2,3,4,5-tetrahydro-1H-pyrido[4,3-b]indole;
2,8-dimethyl-5-{2-[6-(trifluoromethyl)pyridin-3-yl]ethyl}-2,3,4,5-tetrahydro-1H-pyrido[4,3-b]indole;
8-fluoro-2-methyl-5-{2-[6-(trifluoromethyl)pyridin-3-yl]ethyl}-2,3,4,5-tetrahydro-1H-pyrido[4,3-b]indole;
8-chloro-2-methyl-5-{2-[6-(trifluoromethyl)pyridin-3-yl]ethyl}-2,3,4,5-tetrahydro-1H-pyrido[4,3-b]indole;
2-methyl-8-(trifluoromethyl)-5-{2-[6-(trifluoromethyl)pyridin-3-yl]ethyl}-2,3,4,5-tetrahydro-1H-pyrido[4,3-b]indole;
5-[2-(6-fluoropyridin-3-yl)ethyl]-2-methyl-2,3,4,5-tetrahydro-1H-pyrido[4,3-b]indole;
5-[2-(6-fluoropyridin-3-yl)ethyl]-2,8-dimethyl-2,3,4,5-tetrahydro-1H-pyrido[4,3-b]indole;
8-fluoro-5-[2-(6-fluoropyridin-3-yl)ethyl]-2-methyl-2,3,4,5-tetrahydro-1H-pyrido[4,3-b]indole;
5-[2-(2-fluoropyridin-4-yl)ethyl]-2-methyl-2,3,4,5-tetrahydro-1H-pyrido[4,3-b]indole;
5-[2-(2-fluoropyridin-4-yl)ethyl]-2,8-dimethyl-2,3,4,5-tetrahydro-1H-pyrido[4,3-b]indole;
8-fluoro-5-[2-(2-fluoropyridin-4-yl)ethyl]-2-methyl-2,3,4,5-tetrahydro-1H-pyrido[4,3-b]indole;
5-[2-(3-fluoropyridin-4-yl)ethyl]-2-methyl-2,3,4,5-tetrahydro-1H-pyrido[4,3-b]indole;
5-[2-(3-fluoropyridin-4-yl)ethyl]-2,8-dimethyl-2,3,4,5-tetrahydro-1H-pyrido[4,3-b]indole;
8-fluoro-5-[2-(3-fluoropyridin-4-yl)ethyl]-2-methyl-2,3,4,5-tetrahydro-1H-pyrido[4,3-b]indole;
2-methyl-5-{2-[2-(trifluoromethyl)pyridin-4-yl]ethyl}-2,3,4,5-tetrahydro-1H-pyrido[4,3-b]indole;
2,8-dimethyl-5-{2-[2-(trifluoromethyl)pyridin-4-yl]ethyl}-2,3,4,5-tetrahydro-1H-pyrido[4,3-b]indole;
8-fluoro-2-methyl-5-{2-[2-(trifluoromethyl)pyridin-4-yl]ethyl}-2,3,4,5-tetrahydro-1H-pyrido[4,3-b]indole;
2-{5-[2-(5-fluoropyridin-3-yl)ethyl]-1,3,4,5-tetrahydro-2H-pyrido[4,3-b]indol-2-yl}ethanol;
2-{5-[2-(5-fluoropyridin-3-yl)ethyl]-8-methyl-1,3,4,5-tetrahydro-2H-pyrido[4,3-b]indol-2-yl}ethanol; or
2-{8-fluoro-5-[2-(5-fluoropyridin-3-yl)ethyl]-1,3,4,5-tetrahydro-2H-pyrido[4,3-b]indol-2-yl}ethanol.

Some embodiments may include pharmaceutical compositions comprising pyrido[4,3-b]indole derivatives of formula I or the salts and/or solvates thereof as active ingredients. Some compositions may be in the form of a cis-isomer. Pharmaceutically acceptable salts may include hydrochloride salts or dihydrochloride salts. Pharmaceutical compositions may be in aqueous form, tablet form, or other forms. Tablets may further comprise lactose and/or magnesium stearate and/or other components. Pharmaceutical compositions may be administered as doses over a particular period of time or per other regimens. Pharmaceutical compositions may be in the form of a capsule, intravenous formulation, intranasal formulation, transdermal formulation, formulation for muscular injection, syrup, suppository, aerosol, or pessary placed in a pharmaceutically acceptable packing.

Methods of Making

In some embodiments, fluoro-containing pyrido[4,3-b]indole derivatives of formula I may be prepared by nucleophilic addition of a hydrogenated pyrido[4,3-b]indole of formula II to a reactive vinylpyridine of formula III,

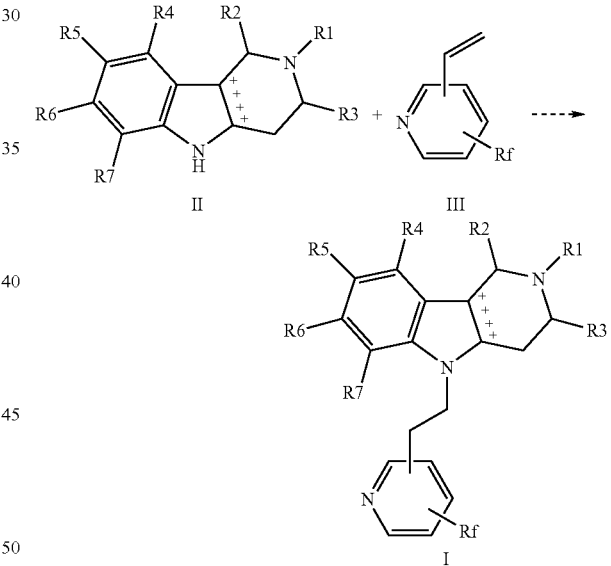

where $R^f$, $R^1$-$R^7$ have the same meaning as given for formula I.

The reaction of a gamma-carboline of formula II with a vinylpyridine of formula III is preferably carried out in a solvent (e.g., DMF, DMSO, HMPTA, NMP, ethanol, etc.) and in the presence of a base (e.g., MeONa, t-BuOK, NaOH, DABCO, tributylamine, CsF, etc.).

Examples of Making

General Method for Synthesis of Gamma-Carbolines II 0.01 mole of arylhydrazine hydrochloride and then 10 ml HCl (conc.) were added to a solution containing 0.01 mole of corresponding piperidone in 10 ml ethanol. The reaction mixture was boiled for six hours to the point of dissolving the solid reagents. The resulting mixture was cooled, 50 ml $H_2O$ was added, and the mixture was brought to pH 9 by the addition of 30% NH$_4$OH. The solid precipitate was filtered, dried and crystallized from hexane.

Preparation of the Intermediate III.

Example 1

2-Fluoro-5-vinylpyridine

A mixture of 7.0 g (0.04 mole) 2-fluoro-5-bromopyridine, 15.3 g (0.048 mole) tributyl(vinyl)stannane, 2.5 g (0.002 mole) tetrakis(triphenylphosphine)palladium in 70 ml toluene was boiled with reflux during 16 hours. Toluene was evaporated with a 30 cm column. The residue was fractionated twice.

Analytic Data:
Yield 67%, by 74-76 C at 30 mm Hg;
$^1$H NMR spectrum (CDCl3);
5.36 d (1H, =CH$_2$, J(HH) 11;
5.76 d (1H, =CH$_2$, J(HH) 17);
6.68 dd (1H, =CH);
6.90 dd (1H, J(HF) 2.3, J(HH)) 8.6);
7.85 ddd (1H, J(HF) 8.7, J(HH) 8.7, J(HH) 2.5);
8.18 d (1H, J(HH) 2.5);
19F NMR spectrum (CDCl3): 8.34 d J 8.

Example 2

3-Fluoro-5-vinylpyridine

A mixture of 7.0 g (0.04 mole) 3-fluoro-5-bromopyridine, 15.3 g (0.048 mole) tributyl(vinyl)stannane, 2.5 g (0.002 mole) tetrakis(triphenylphosphine)palladium in 70 ml toluene was boiled with reflux during 16 hours. Toluene was evaporated with a 30 cm column. The residue was fractionated twice.

Analytic Data:
Yield 60%, by 76-77 C at 30 mm Hg;
$^1$H NMR spectrum (CDCl3);
5.50 d (1H, =CH$_2$, J(HH) 11;
5.89 d (1H, =CH$_2$, J(HH) 17);
6.76 m (1H, =CH);
7.48 ddd (dt) (1H, J(HF) 9.7, J(HH)) 2.3);
8.40 d (1H, J 2.3);
8.48 dd (1H, J(HH) 1.2);
19F NMR spectrum (CDCl3): 49.80 d J 9.7.

General Methods for Exemplary Embodiments 1 mmole of carboline II, 1 mmole of 3-fluoro-5-vinylpyridine III, 200 mg CsF, and 5 mg hydroquinone in 1.5 ml DMSO were heated with stirring at 135-140 C during 8 h. DMSO and vinylpyridine were removed at vacuum at 3 mm Hg; then, the product was extracted with CH$_2$Cl$_2$. The solvent was evaporated and the residue was isolated by chromatography on silica gel (60 mesh) with CH$_3$OH/CHCl$_3$ (1/5) as eluent.

Methods of Use

Some embodiments comprise treatments with these compounds, which includes administering to a mammal (including a human) an effective amount of a pyrido[4,3-b]indole derivative of formula I. Compounds of formula I are believed to be of potential use in the treatment or prophylaxis of neurological disorders including AD, mild cognitive impairment, senile and vascular dementia, HD, ALS, Parkinson's disease, AIDS-related dementia, ischaemic cerebral pathologies, neuropathic pain, ADHD (attention deficit disorder/hyperactivity syndrome), eating disorders such as anorexia and bulimia, panic attacks, withdrawal from drug abuse such as cocaine, ethanol, nicotine and benzodiazepines, schizophrenia (in particular the cognitive deficit of schizophrenia), stroke and also disorders associated with spinal trauma and/or head injury. Compounds of formula I may also be useful for the treatment of borderline personality disorder and obesity. Compounds of formula I also may be applied to healthy aging and wellness in dogs and other companion animals.

Compounds of formula I are believed to be of potential use as geroprotectors, which may be applied for slowing aging, prolonging lifespan of an individual or cells in an individual, and/or improving quality of life of an individual developing or having a risk of developing age-associated manifestations and/or pathologies. The compounds may also have potential use for treatment of mild cognitive impairment, senile and vascular dementia, AIDS-related dementia, ischaemic cerebral pathologies, neuropathic pain, ADHD (attention deficit disorder/hyperactivity syndrome), eating disorders such as anorexia and bulimia, panic attacks, withdrawal from drug abuse such as cocaine, ethanol, nicotine and benzodiazepines, schizophrenia (in particular the cognitive deficit of schizophrenia), stroke and also disorders associated with spinal trauma and/or head injury.

The various exemplary compounds presented herein may useful in treating conditions characterized at least in part by a cholinergic deficit state, such as myasthenia gravis, tardive dyskinesia, or dementia associated with Down's syndrome. The compounds may also be used as "pharmacological tools" for an investigation of the mechanism of protection against neurodegeneration disorders in vivo or in vitro. The compounds may be administered orally, intramuscularly, subcutaneously, rectally or topically.

FIGS. 1A-1B is a table of yields and melting points for multiple exemplary compounds corresponding to structure nos. one (1) through (15). Shown in the table (from left to right) are structure, yield based on nuclear magnetic resonance percentage in a reaction mixture, isolated yield (base %), and melting points for hydrochloride salts (degrees Celsius) for exemplary compounds corresponding to structure nos. (1) through (15).

FIGS. 2A-2C is a table of NMR data for multiple exemplary compounds corresponding to structure nos. one (1) through (15).

Effects of exemplary compounds, such as those shown in FIGS. 1A-1B and FIGS. 2A-2C, were studied in preclinical pharmacology, ex vivo, in vitro, and in vivo.

Ex vivo, exemplary compounds have been demonstrated to inhibit total and specific glutamate-stimulated calcium-ion uptake in rat brain synaptosomes in a sub-micromolar concentration range.

In vitro, exemplary compounds have been demonstrated to inhibit selectively butyrylcholinesterase ("BuChE") in a sub-micromolar concentration range. Acetylcholinesterase ("AChE") predominates in a healthy brain, with BuChE considered to play a minor role in regulating brain acetylcholine (ACh) levels. However, BuChE activity progressively increases in patients with AD, while AChE activity remains unchanged or declines [Geula C., Mesulam M. Cholinesterases and the pathology of Alzheimer disease. Alzheimer Dis. Assoc. Disord. 1995; 9 Suppl. 2:23-8]. Research indicates that BuChE is found in significantly higher quantities in AD plaques than in plaques from age-matched non-demented brains. Moreover, BuChE was found to alter the aggregation of beta-amyloid peptide that is a neurotoxic factor, inducing neurodegenerative processes in the AD neurons [Greig N., et. al. Selective butyrylcholinesterase inhibition elevates brain acetylcholine, augments learning and lowers Alzheimer beta-amyloid peptide in rodent. Proc. Natl. Acad. Sci. U S A. 2005; 102(47):17213-8]. It has been shown that BuChE may play an important role in the in vivo regulation of synaptic concentrations of acetylcholine in the brains of AD patients. Inhibition of brain BuChE represents a new drug target for AD treatment [Greig N. H., Lahiri D. K., Sambamuti K. Butyrylcholinesterase: an important new target in Alzheimer's disease therapy. Int. Psychogeriatr. 2002; 14 Suppl 1:77-91].

In vitro, it was found that surprisingly, some exemplary compounds are functional antagonists of serotonin 5-HT6 receptors, which are new, attractive targets for cognition enhancement [Mitchell E. S., Neumaier J. F. 5-HT6 receptors: a novel target for cognitive enhancement. Pharmacol. Ther. 2005; 108(3):320-33]. 5-HT6 receptors are present selectively in brain regions that are associated with learning and memory, and blockade of their function increases ACh and glutamate-mediated neurotransmission, and enhances cognitive processes [Holenz J., et. al. Medicinal chemistry strategies to 5-HT6 receptor ligands as potential cognitive enhancers and antiobesity agents. DDT 2006; 7/8:283-96].

In vivo, some of the exemplary compounds have been demonstrated to prevent the development of NMDA-induced convulsion in experimental animals. The results indicate strong anti-NMDA properties of the exemplary compounds tested.

In vivo, some of the exemplary compounds demonstrated memory-enhancing properties in the object-recognition task ("ORT") as discussed herein, which is a method to measure a specific form of episodic memory in rodents. Solvent-treated mice in the 1 h retention inter-trial interval condition did not discriminate between the novel and the familiar object (discrimination index was equal to zero), while mice treated with exemplary compounds (in doses ranging from 0.010 mg/kg-5.0 mg/kg) attained a good object-recognition memory performance.

Thus, exemplary compounds may be advantageously used for the treatment of neurological disorders, neurodegenerative diseases and obesity, for instance AD or HD, owing to their unique combined antagonist activity on the NMDA receptors, antagonist action on the 5-HT6 receptors and inhibitor properties on the enzyme BuChE.

Biological Results

Object recognition test as a method for research on the effects of some exemplary compounds on memory in mice.

The object recognition test is based on a spontaneous behavior of rats and mice to explore a novel object or a new localization of an object more often than a familiar one. This test was first developed for rats [Ennaceur A., Delacour J. A new one-trial test for neurobiological studies of memory in rats. 1: behavioral data. Behav. Brain Res. 1988; 31:47-59]. Thereafter, various researchers have shown that the test is also suitable for assessing memory performance in mice [e.g., Dodart J. C., Mathis C., Ungerer A. Scopolamine-induced deficits in a two-trial object recognition task in mice. NeuroReport 8 (1997), pp. 1173-1178]. The object recognition test is divided into two tests: a test of recognition of a new localization of an object that is used for research on spatial memory, and a test of recognition of a new object that is used for research on non-spatial memory.

Twenty (20) to twenty-two (22) month-old female mice (old mice) and four (4) to six (6) month-old male mice (young mice) of C57BL/6 strain were used. The animals were housed five per cage under a normal light cycle (12×12, light on at 8:00 AM) and with free access to water and food. The training box was made of white, opaque organic glass with dimensions of 48×38×30 cm. Two kinds of plastic items were used as objects for recognition: a white cylinder (d=4 cm, h=2.8 cm), and a black, three-edged prism (2.5×2.5×3.5 cm and h=3.4 cm). Care was taken to avoid olfactory stimuli by cleaning the objects and box carefully. Two (2) to three (3) min before the mice were placed into the box, the objects and the box were wiped with 85% ethanol. Animals were always placed in the middle of the training box.

Referring again to FIGS. 1A-1B and FIGS. 2A-2C, the mice were injected intraperitoneally with some of the various exemplary compounds shown in the figures, or with the vehicle (solvent) alone in the same volume, one hour before the recall trial.

Procedures.

Adaptation.

On the first day of the experiment, the mice were handled in the research room for 20 to 30 min for acclimatization. Then, one by one, the mice were habituated to the training box by being placed into the box without any object for 20 min to explore the box, and were returned to their cages.

Training (Acquisition).

On the next day, the same mice were brought into a research room. After 20-30 min of acclimatization, each mouse was placed into an empty box for one minute. Then, the mouse was removed from the training box. Two identical objects (white cylinders) were placed approximately 5 inches distant from two adjacent corners of the box and immediately an animal was returned to the box. The time of exploring of each individual object was registered separately with the help of two electronic stop-watches (to within 0.1 sec). The behavior of each animal was observed through a mirror. Exploration was operationally defined as directing the nose to the object from a distance less than 2 cm, or touching the object with the nose. The duration of the training trial was 5, 10, 15 and 20 minutes.

Testing (Recall).

The delay interval conditions (the interval between training and testing) were 1, 4 or 24 hours, depending on the experimental problem. Testing was performed the same way as training, but one of the two familiar objects was changed to the new object (black prism).

When the recognition of a new localization of an object improved, the same experimental sequence was performed, except that only the localization of one of the familiar objects was changed in the testing session.

Statistical Analysis.

A significant variability of object exploration times between animals was measured. The ratio of object-exploration times was calculated as follows: each object-exploration time was divided by the sum of both of the object-exploration times during the same testing session, and expressed in percent:

$$(t_{new} \times 100\%)/(t_{familiar}+t_{new})$$

The data were analyzed using a one-way analysis of variance followed by a Student's t-test.

The following examples demonstrate the results obtained:

Example 3

Figure 3:
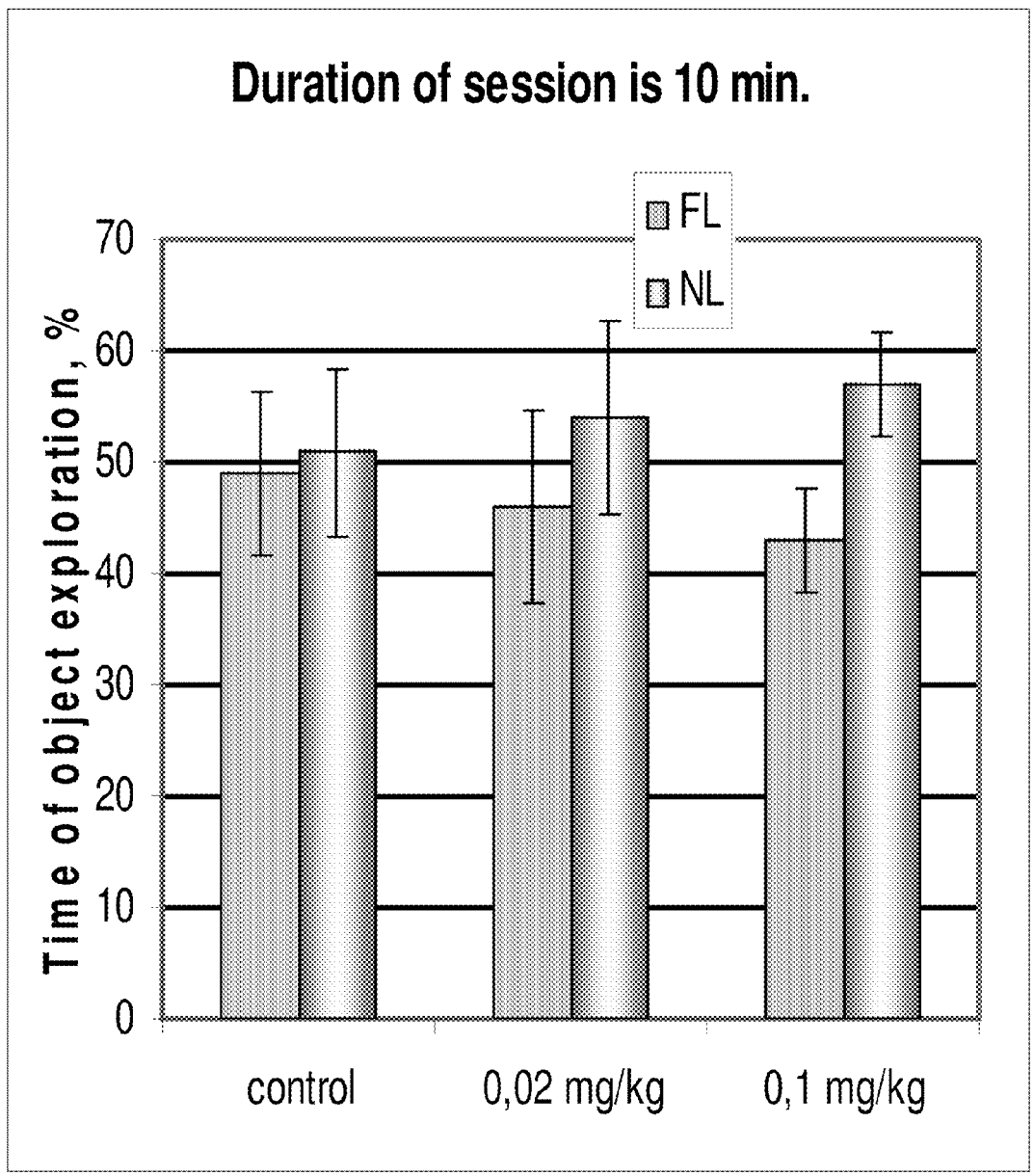
FIG. 3 shows test results obtained with respect to the influence of one exemplary compound on object exploration in familiar and new localizations.

FIG. 3 shows test results obtained with respect to the influence of one exemplary compound on object exploration in familiar and new localizations. A control group of mice explored the object in a familiar localization for approximately 49.1+/−7.4% of a time period, and explored the object in a new localization for approximately 50.9+/−7.4% of the time period when tested at 48 hours after training. These results indicate that the mice did not remember where the objects had been placed during training. In contrast to a control group, mice treated prior to training with 0.1 mg/kg of compound 5 spent less time exploring the object in a familiar localization, approximately 43.0 +/−4.6% of the time period, and in more time exploring the object in a new localization, 57+/−4.6% of the time period (P=0.003). This indicates that in this test group, the animals remembered the object in a familiar localization, and spent more time exploring the object located in a new place. Results with the 0.02 mg/kg injection of compound 5 did not differ significantly from the control.

Example 4

Figure 4:
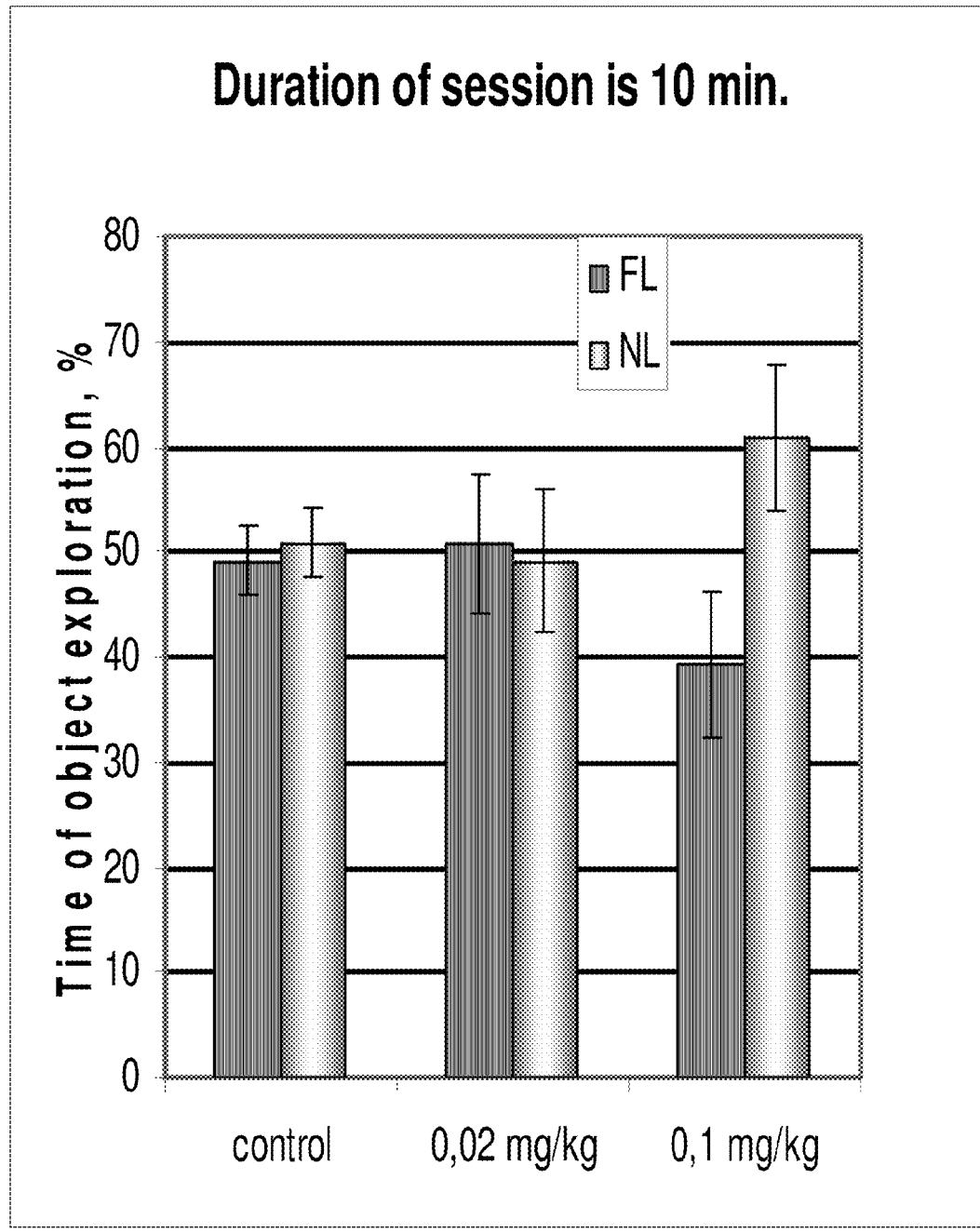
FIG. 4 shows test results obtained with respect to the influence of another exemplary compound on object exploration in familiar and new localizations.

FIG. 4 shows test results obtained with respect to the influence of another exemplary compound on object exploration in familiar and new localizations. The same high activity was found for compound 8. Animals treated with 0.1 mg/kg of compound 8 spent 60.8+/−6.9% of their object exploration time with the object in a new localization, and 39.2+/−6.9% of their object exploration time with the object in a familiar localization (P=0.002). However, the discrimination ratio of mice treated with 0.02 mg/kg was not different from that of the control mice.

These results suggest that compounds 5 and 8 possess high activating influence on learning and memory, which lasts no less than 48 hours after training. These compounds appear to be approximately 25 times more effective than memantine as memory stimulating agents (and memantine is a well-known medical treatment for Alzheimer's disease).

Example 5

Inhibition of serotonin-6 receptor (5-TH6), and butyrylcholine esterase (BuChE) as an assessment of the potential benefit of the compounds in the therapy of neurodegenerative diseases.

Procedure.
Butyrylcholine Esterase Assay.
The assay was conducted as follows [Ellman G. L., Courtney K. D., Andres Jr. V., and Featherstone R. N. A new and rapid colorimetric determination of acetylcholinesterase activity. Biochem. Pharmacol. 1961, 7:88-95]:

| | |
|---|---|
| Enzyme source: | human serum; |
| Substrate: | 560 uM S-Butyrylthiocholine |
| Vehicle: | 1% DMSO; |
| Pre-Incubation time of the enzyme: | 15 min at 25 C.; |
| Incubation time of the compound with the enzyme: | 2 hours at 25 C.; |
| Compound concentration: | 10 uM; |
| Incubation buffer: | 0.1 M sodium phosphate buffer, pH 7.4, 0.5% Tween 20; |
| Quantitation method: | spectrophotometric quantitation of thiocholine. |

Binding with 5-HT6 Receptor.
The assay was conducted as follows [Monsma F. J., Jr, Shen Y., Ward R. P., Hamblin M. W., and Sibley D. R. Cloning and Expression of a novel serotonin receptor with high affinity for tricyclic psychotropic drugs. Mol. Pharmacol. 1993, 43: 320-327]:
Receptor source: human recombinant HeLa cells;
Ligand: 1.5 nM [3H]-lysergic acid diethylamide (LSD);
Vehicle: 1% DMSO;
Incubation time: 2 hours at 37 C;
Incubation buffer: 50 mM Tris-HCl, pH 7.4, 150 mM NaCl, 2 mM ascorbic acid, 0.001% BSA;
Compound concentration: 10 uM;
Non-specific ligand: 5 uM serotonin (5-HT);
Quantitation method: radioligand binding

| # | Structure | 5-HT6 % of inhibition | BuChE % of inhibition |
|---|---|---|---|
| 1 | 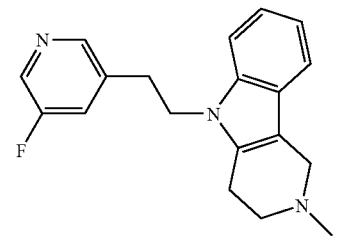 | 90 | 75 |
| 2 | 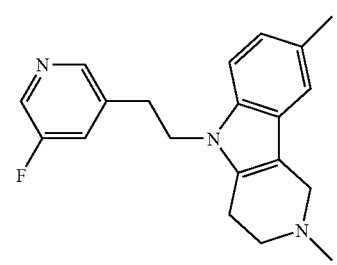 | 102 | 87 |

-continued
| # | Structure | 5-HT6 % of inhibition | BuChE % of inhibition |
|---|---|---|---|
| 3 | 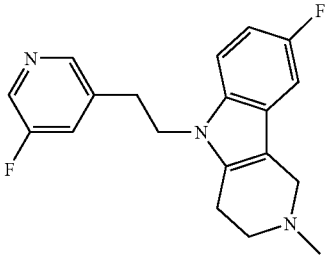 | 99 | 58 |
| 4 | 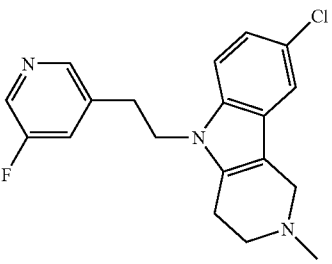 | 103 | 91 |
| 5 | 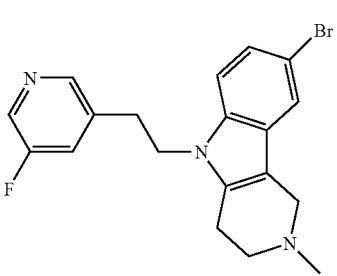 | 103 | 96 |
| 6 | 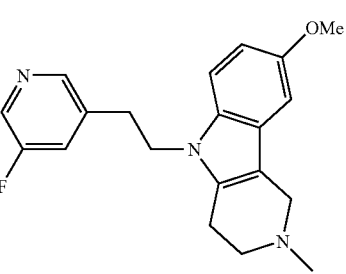 | 96 | 99 |
| 8 | 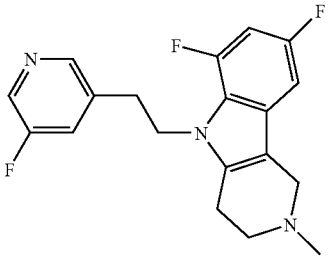 | 91 | 31 |

-continued

| # | Structure | 5-HT6 % of inhibition | BuChE % of inhibition |
|---|---|---|---|
| 9 | 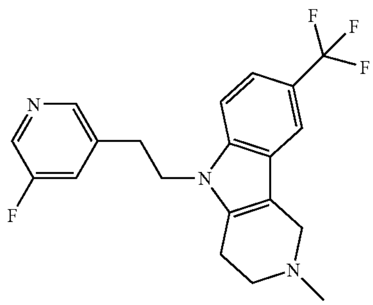 | 103 | 95 |
| 10 | 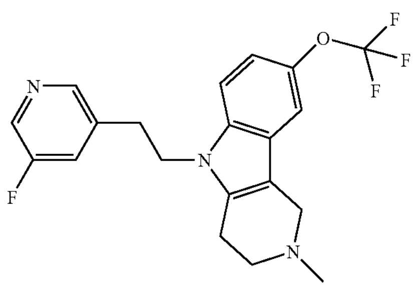 | 95 | 100 |
| 11 | 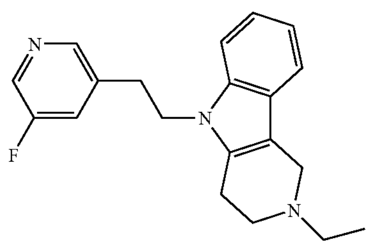 | 77 | 66 |
| 12 | 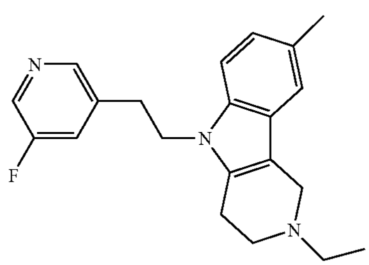 | 101 | 89 |
| 14 | 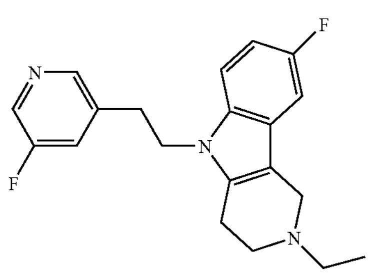 | 88 | 53 |

-continued

| # | Structure | 5-HT6 % of inhibition | BuChE % of inhibition |
|---|---|---|---|
| 15 | 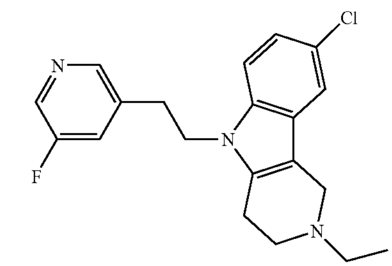 | 99 | 94 |
| 4-01 | 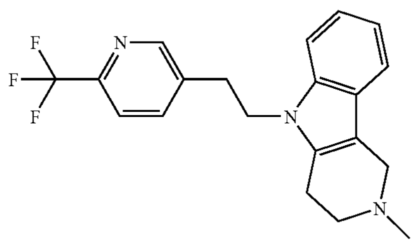 | 67 | 65 |
| 4-02 | 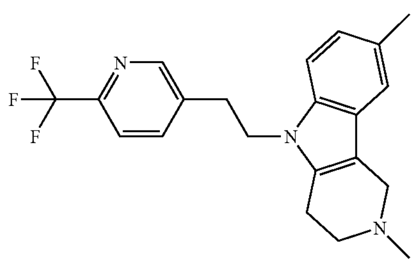 | 97 | 95 |
| 4-03 | 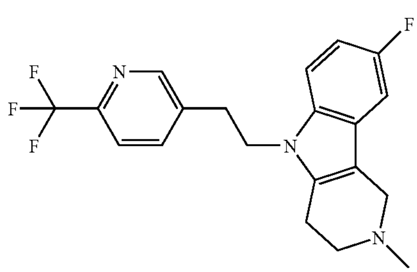 | 72 | 34 |
| 4-04 | 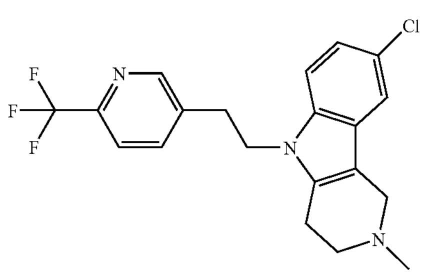 | 100 | 97 |
| I. 4-06 | 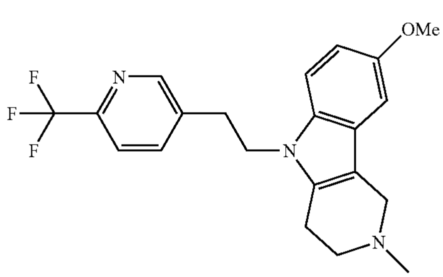 | 72 | 99 |

-continued

| # | Structure | 5-HT6 % of inhibition | BuChE % of inhibition |
|---|---|---|---|
| 4-07 | 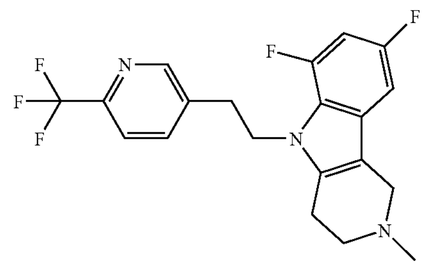 | 79 | 20 |
| 4-08 | 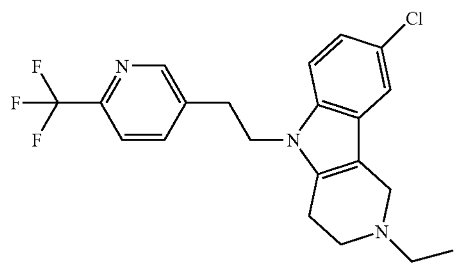 | 77 | 100 |

Example 6

The various new and non-obvious exemplary compounds (and new and non-obvious methods of making them) presented herein are believed to have dramatically improved functional in vitro and in vivo properties over an existing compound commonly known as dimebon. Among other things, the compounds presented herein are believed to have an improved half-life and/or sustainability within mammals (e.g. humans), representing a dramatic achievement for establishing and maintaining active, therapeutic, and/or pharmacologically effective amounts within mammals. Accordingly, data based upon dimebon may provide guidance for the various exemplary methods described herein, including new and non-obvious combination or "cocktail" methods involving the compounds presented herein and already known compounds, such as donepezil.

Dimebon drew notice for its ability to improve AD patients for at least 12 months on all of five cognitive measures [see, e.g. "Chicago: Dimebon Safe for 18 Months," Esther Landhuis and Gabrielle Strobel, Alzheimer Research Forum, 8 Aug. 2008]. Data from the International Conference on Alzheimer's Disease (ICAD), held in July 2008 included information suggesting that dimebon acts to stabilize mitochondria. Such a target is distinct from those of currently available AD drugs that work by inhibiting acetylcholinesterases (enzymes that break down a key learning/memory neurotransmitter) or NMDA receptors (proteins whose hyperactivation may underlie the degeneration of cholinergic cells). Dimebon, too, acts on these molecules, as shown in earlier work by Russian scientists (Bachurin et al., 2001; Bachurin et al., 2003). Because potency is a critical factor in drug development, researchers at Medivation have confirmed the earlier acetylcholinesterase findings in two sets of experiments—one using recombinant enzyme and another using fresh blood samples from three volunteers. In these follow-up studies presented at ICAD, dimebon blocked acetylcholinesterase activity with a half-maximal inhibitory concentration (IC50) in the 31-72 micro-molar range—several thousand-fold lower than that of the widely prescribed anti-cholinesterase drug donepezil. In NMDA receptor binding assays, dimebon's inhibition constant (Ki—a related measure of potency, defined as the concentration of test compound required to bind 50 percent of receptors in the absence of agonist) was 97 micro-molar, compared with 0.5 micro-molar for the AD drug memantine.

Additionally, dimebon functions differently from current AD drugs in that its side effect profile in human studies shows that less than 3 percent of clinical trial participants who took dimebon reported gastrointestinal problems. In contrast, it is believed that more than 20 percent of AD patients taking donepezil routinely experience such symptoms. Mitochondrial involvement as one of dimebon's mechanisms was suggested by enzyme inhibition assays, cell-based activity assays, kinase profiling, and commercial compound screening services. Previously, mitochondrial dysfunction was linked to aging and neurodegenerative diseases, including Alzheimer's disease. As the primary power plants of the cell, mitochondria churn out toxic compounds that may accelerate beta amyloid plaque production in AD mouse models. In transgenic mice with a mitochondrial enzyme defect leading to buildup of harmful aldehydes, age-related neurodegeneration kicked-in and led to early death.

Dimebon's potential mitochondrial activities have been studied by researcher treating SK—N—SH human neuroblastoma cells with ionomycin, which reduces the electrochemical gradient across mitochondrial membranes, triggering apoptosis. Mitochondrial function was assessed using JC-1, a dye that fluoresces red when it accumulates in healthy mitochondria and green when forced to remain in the cytoplasm due to collapsed mitochondrial membrane potentials. This allowed the researchers to gauge mitochondrial health as a percentage of cells fluorescing red versus green. The red/green ratio for cells hit with ionomycin dropped to 70 percent of that seen for untreated cells. Picomolar concentrations of dimebon brought the ratio up to 85-90 percent of control cells in a concentration-dependent fashion. As measured in MTT (3-[4,5-dimethyl-2-thiazolyl]-2,5-diphenyl-2H-tetrazolium bromide) assays, ionomycin treatment reduced cell viability to 40 percent of control cells, and picomolar dimebon restored survival to 75-85 percent. Separate experiments examined mitochondrial function in a related neuroblastoma line (SH—SY5Y) using a different probe (tetramethyl rhodamine methyl ester, or TMRM). With this, too, the researchers reported that pre-treatment with one nano-molar dimebon protected cells from ionomycin-induced stress. Together, these findings suggest that dimebon's mitochondria-stabilizing effects are potent and correlate with improved cell viability.

Because dendritic mitochondria may be important for synaptic plasticity, a process critical for learning and memory, researchers examined dimebon's effects on the growth of neurites. In primary rat cortical neurons cultured for three days with either brain-derived neurotrophic factor (BDNF) or dimebon, picomolar concentrations of dimebon increased neurite outgrowth as well as did BDNF applied at its maximally effective concentrations.

Also at ICAD, Jeffrey Cummings of the University of California, Los Angeles, presented clinical results of the six-month open-label extension of dimebon's Phase 2 trial in Russia, which brought exposure to the drug out to 18 months in these patients with mild to moderate AD. In this extension, patients who had been on dimebon during the blinded phase continued on dimebon. Patients who had been randomized to placebo crossed over to dimebon. This created, at the 18-month time point, a mixture of people who had been on dimebon for 18 months with a slight improvement over baseline at 12 months, and of other people who been declining in the placebo group for 12 months. People who had been on dimebon all along declined somewhat after 12 months, but ended the 18-month time point with only an ADAS-Cog change of about minus 2 from the start of the trial. They appeared to hold their own, i.e., around baseline, on a psychiatric rating scale. People who had previously been on placebo at 18 months remained stable at the lower level of cognitive function at which they had ended their 12 months on placebo. Results also indicated no safety or tolerability issues. The one side effect reported more frequently in the treatment group was depression. This depression was self-reported, not measured by depression scales. Accordingly, it raised a question: did the people become depressed because of improving their cognition to the point of understanding their still-difficult condition? Consequently, the administration of an antidepressant, such as a tricyclic antidepressant, in combination with some or all of the exemplary compounds presented herein may be warranted.

Research performed by Bachurin S O, Shevtsova E P, Kireeva E G, Oxenkrug G F, and Sablin S O (see "Mitochondria as a target for neurotoxins and neuroprotective agents," Ann NY Acad. Sci. 2003 May; 993:334-44, discussion 345-9) indicates that mitochondrial permeability transition pores represent a multiprotein complex that includes components of both inner and outer membrane. The pores regulate transport of ions and peptides in and out of the mitochondria. Their regulation is associated with a general mechanism for maintaining Ca(2+) homeostasis in the cell and apoptosis. Various pathologic factors may induce a pathologic activation of the permeability transition and an irreversible opening of mitochondria pores. This event may be a major step in the development of neurotoxicity and neurodegeneration. Their research explores the effect of MPP(+) and beta-amyloid fragment 25-35, which are neurotoxins that are known to generate Parkinson's-like syndrome and Alzheimer's disease, on the regulation of the mitochondrial pores. Both neurotoxins induce opening of mitochondrial pores, which is prevented by cyclosporin A, a specific inhibitor of the permeability transition. The effect of MPP(+) and beta-amyloid may be also prevented by an endogenous precursor of melatonin, N-acetylserotonin, by an anti-Alzheimer's medication tacrine, and by dimebon, which is in development as an agent for the therapy of Alzheimer's disease and other types of dementia. Their research illustrates that the effect on mitochondrial pores may be an important aspect of the mechanism of neurotoxicity. Substances that may prevent opening of mitochondrial pores induced by neurotoxins may preserve the mitochondrial function and, thus, may have potential as neuroprotective agents.

Example 7

The various new and non-obvious exemplary compounds (and new and non-obvious methods of making them) presented herein are believed to have dramatically improved functional in vitro and in vivo properties over an existing compound commonly known as dimebon. Among other things, the compounds presented herein are believed to have an improved half-life and/or sustainability within mammals (e.g. humans), representing a dramatic achievement for establishing and maintaining active, therapeutic, and/or pharmacologically effective amounts within mammals. Accordingly, data based upon dimebon may provide guidance for the various exemplary methods described herein.

Dimebon has an anti-calcium activity, in particular it was found it is capable of inhibiting the entry of calcium ions into nerve cells, which was induced by the activation of glutamate receptors. On the other hand, it is known that hyperaccumulation of calcium ions in cells induces a cascade of degenerative processes, which accompany the process of ageing and a development of corresponding degenerative diseases. A disturbance in calcium homeostasis is the basis for a so-called calcium theory of ageing and dementia [Calcium Hypothesis of Ageing and Dementia. Ann. N.Y. Acad. Sci., 1994, v. 747].

It was also discovered that dimebon slowed aging, prolonged life, reduced occurrence of hair loss, and reduced cataracts in aging mice. Thus, because of the new unexpected properties which do not follow from the structure of dimebon, compounds described herein may be used as geroprotectors. The definition "geroprotective activity," means a biological activity that slows down ageing and/or prolongs life and/or increases or improves the quality of life via a decrease in the amount and/or the level of intensity of pathologies or conditions that are not life-threatening but are associated with the aging process and which are typical for elderly people. Pathologies or conditions that are not life-threatening but are associated with the aging process include such pathologies or conditions as loss of sight (cataract), deterioration of the dermatohairy integument (alopecia), and an age-associated decrease in weight due to the death of muscular and/or fatty cells.

Methods such as a method of slowing aging may comprise the administration to an individual (such as a human patient) of a pharmacological tool that contains the effective amount of dimebon in a dose of between 0.1 and 10 mg/kg of the body weight, at least once a day and during the period of time, which is required to achieve the therapeutic effect. In other variations, the daily dose (or other dosage frequency) is between about 0.1 and about 8 mg/kg; or between about 0.1 to about 6 mg/kg; or between about 0.1 and about 4 mg/kg; or between about 0.1 and about 2 mg/kg; or between about 0.1 and about 1 mg/kg; or between about 0.5 and about 10 mg/kg; or between about 1 and about 10 mg/kg; or between about 2 and about 10 mg/kg; or between about 4 to about 10 mg/kg; or between about 6 to about 10 mg/kg; or between about 8 to about 10 mg/kg; or between about 0.1 and about 5 mg/kg; or between about 0.1 and about 4 mg/kg; or between about 0.5 and about 5 mg/kg; or between about 1 and about 5 mg/kg; or between about 1 and about 4 mg/kg; or between about 2 and about 4 mg/kg; or between about 1 and about 3 mg/kg; or between about 1.5 and about 3 mg/kg; or between about 2 and about 3 mg/kg; or between about 0.01 and about 10 mg/kg; or between about 0.01 and 4 mg/kg; or between about 0.01 mg/kg and 2 mg/kg; or between about 0.05 and 10 mg/kg; or between about 0.05 and 8 mg/kg; or between about 0.05 and 4 mg/kg; or between about 0.05 and 4 mg/kg; or between about 0.05 and about 3 mg/kg; or between about 10 kg to about 50 kg; or between about 10 to about 100 mg/kg or between about 10 to about 250 mg/kg; or between about 50 to about 100 mg/kg or between about 50 and 200 mg/kg; or between about 100 and about 200 mg/kg or between about 200 and about 500 mg/kg; or a dosage over about 100 mg/kg; or a dosage over about 500 mg/kg. In some embodiments, a daily dosage of dimebon is administered. The daily dosage for dimebon can be a 10 mg/kg dosage.

Dimebon may be administered for a sustained period, such as at least about one month, at least about 2 months, at least about 3 months, at least about 6 months, or at least about 12 months or longer. Other dosing schedules may also be followed. For example, the frequency of the administration may vary. The dosing frequency can be a once weekly dosing. The dosing frequency can be a once daily dosing. The dosing frequency can be more than once weekly dosing. The dosing frequency can be more than once daily dosing, such as any one of 2, 3, 4, 5, or more than 5 daily doses. The dosing frequency can be 3 times a day. The dosing frequency can be three times a week dosing. The dosing frequency can be a four times a week dosing. The dosing frequency can be a two times a week dosing. The dosing frequency can be more than once weekly dosing but less than daily dosing. The dosing frequency can be a once monthly dosing. The dosing frequency can be a twice weekly dosing. The dosing frequency can be more than once monthly dosing but less than one weekly dosing. The dosing frequency can intermittent (e.g., one daily dosing for 7 days followed by no doses for 7 days, repeated for any 14 day time period, such as 2 months, 4 months, 6 months or more). The dosing frequency can be continuous (e.g., one weekly dosing for continuous weeks). Any of the dosing frequencies can be used with any dosage amount, for example, any of the dosing frequencies can employ a 10 mg/kg dosage amount. Any of the dosing frequencies can employ any of the compounds described herein together with any of the dosages described herein, for example, the dosing frequency can be a three times daily 10 mg/kg dose of dimebon.

Compounds as described herein may be administered to mammals in a form of generally accepted oral compositions, such as tablets, coated tablets, gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical preparations may contain preservatives, solubilizers, stabilizers, re-wetting agents, emulgators, sweeteners, dyes, adjusters, salts for the adjustment of osmotic pressure, buffers, coating agents or antioxidants. Preparations may also contain other substances, which have valuable therapeutic properties. Therapeutic forms may be represented by a usual standard dose and may be prepared by a known pharmaceutical method. Suitable formulations can be found, e.g., in Remington's Pharmaceutical Sciences, Mace Publishing Company, Philadelphia, Pa., (2000), which is incorporated herein by reference. Any of the compounds described herein can be formulated in a tablet in any dosage form described, for example, dimebon or a pharmaceutically acceptable salt thereof can be formulated as a 10 mg tablet. Any of the compounds described herein can be formulated in any dosage as a sustained release formulation. Various embodiments described herein also provides for a sustained release devise, for example a transdermal patch or an implantable devise comprising as the active ingredient any one of the compounds described herein in any total amount such that the individual receives an effective amount of compound during the sustained release period. The technical result, that may be achieved after the application of the present invention, may be a slowing of aging, and/or a significant prolongation of life, and/or an improvement of the quality of life via a decrease in the amount and/or the level of intensity of pathologies or conditions that are not life-threatening but are associated with the aging process, such as loss of sight (cataract), deterioration of the dermatohairy integument (alopecia), an age-associated decrease in weight due to the death of muscular and/or fatty cells.

Embodiments described herein further provide kits for carrying out the various methods of the invention, which comprises one or more compounds described herein. The kits may employ any of the compounds disclosed herein. The kits may be used for any one or more of the uses described herein, and, accordingly, may contain instructions for any one or more of the following uses: slowing aging (such as delaying the onset or slowing the progression of an age-associated or age-related manifestation and/or pathology or condition), prolonging lifespan of an individual, prolonging lifespan of cells in an individual, improving quality of life of an individual, and decreasing risk of developing an age-related condition, such as a non-life-threatening age-related pathology or condition.

Kits generally comprise suitable packaging. The kits may comprise one or more containers comprising any compound described herein. Each component (if there is more than one component) can be packaged in separate containers or some components can be combined in one container where cross-reactivity and shelf life permit. The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

Example 8

The various new and non-obvious exemplary compounds (and new and non-obvious methods of making them) presented herein are believed to have dramatically improved functional in vitro and in vivo properties over an existing compound commonly known as dimebon. Among other things, the compounds presented herein are believed to have an improved half-life and/or sustainability within mammals (e.g. humans), representing a dramatic achievement for establishing and maintaining active, therapeutic, and/or pharmacologically effective amounts within mammals. Accordingly, data based upon dimebon may provide guidance for the various exemplary methods described herein.

Determination of Calcium Blocking Properties of Dimebon.

Evaluation of the calcium-blocking properties of dimebon was conducted with P2-fraction of synaptosomes, which were isolated from the brain of newborn (8-11 days) rats according to the protocol described in [Bachurin et al. Neuroprotective and cognition enhancing properties of MK-801 flexible analogs. Structure-activity relationships./Ann. N.Y. Acad. Sci., 2001, v. 939, pp. 219-235]. In this test, the ability of the compounds to inhibit a specific uptake of calcium ions via ion channels associated with glutamate receptors was determined.

Synaptosomes were placed into the incubation buffer A (132 mM NaCl, 5 mM KCl, 5 mM HEPES) and were kept at 0 degrees Celsius ("C") during the entire experiment. Aliquots of synaptosomes (50.mu.l) were placed in the media A, containing investigated compounds and a preparation of the radiolabeled calcium, $^{45}Ca$. The calcium uptake was stimulated by the introduction into the media of the 20.mu.l of the 10 mM solution of glutamate. After a 5 min incubation at 30 C, the reaction was interrupted by a filtration through GF/B filters, which were then triple washed with the cold buffer B (145 mM KCl, 10 mM tris, 5 mM trilon B). Then, filters were subjects for the detection of the radiolabeled calcium. The measurement was conducted using a scintillation counter 'SL-4000 Intertechnic'. The initial screening was conducted with a concentration of each compound of 5.mu.M. A specific calcium uptake was calculated using the following equation $K(43/21)=[(Ca4-Ca3)/(Ca2-Ca1)]*100\%$ where: Ca1 is a calcium uptake in a control experiment (no glutamate or test compound added); Ca2 is a calcium uptake in the presence of glutamate only (Glutamate Induced Calcium Uptake—GICU); Ca3 is a calcium uptake in the presence of a test compound only (no glutamate added); Ca4 is a calcium uptake in the presence of both glutamate and a test compound. Dimebon exhibited pronounced calcium-blocking properties. This suggests that according to the described above ageing and dementia hypothesis, dimebon may have a potential as a geroprotector.

Example 9

The various new and non-obvious exemplary compounds (and new and non-obvious methods of making them) presented herein are believed to have dramatically improved functional in vitro and in vivo properties over an existing compound commonly known as dimebon. Among other things, the compounds presented herein are believed to have an improved half-life and/or sustainability within mammals (e.g. humans), representing a dramatic achievement for establishing and maintaining active, therapeutic, and/or pharmacologically effective amounts within mammals. Accordingly, data based upon dimebon may provide guidance for the various exemplary methods described herein Data on the Activity of Dimebon as a Geroprotector.

Dimebon was evaluated as an agent that prolongs life and improves the quality of life (characterized by changes in the amount of pathologies that accompany ageing) in the laboratory animals.

Experiments were conducted with C57/B female mice, starting from their age of 12 months. Mice were kept on cells, 10 animals per a cell. Both control and experimental group included 50 animals in each group. Animals had a free access to food and water. The day-night cycle was 12 hours.

Prior to the experiment, daily and weekly water consumption by the animals in one cell was measured. Dimebon was added in water in such amount that each animal would consume 3 mg/kg of Dimebon per day in average. Bottles with water containing Dimebon were replaced every 7 days. Animals in the control group were receiving pure water.

Prior to the experiment, all the animals were weighed, and an average weight was determined in every group, every cell, as well as the weight of all animals in every cell. The condition of skin, hair, and eyes were also determined by visual inspection. All animals appeared healthy and did not have any visible lesions prior to the experiment. Evaluation of all these parameters was conducted on a monthly basis.

Statistics were calculated using Student T-test and 'Chi-squared' criteria.

Results.

Lifespan.

Evaluation of the parameter of the length of life was conducted employing methods used in demography. This parameter was a probability of death in every age group. During the entire experiment the number of animals in the experimental group was greater than in the control group. In other words, the probability of death was lower in all age groups in animals that were receiving dimebon. In age groups of 20-23 months this difference was statistically significant ($P<0.05$).

Dynamics in Weight of Animals.

A decrease in the animal weight was observed during the entire experiment in the control group. This is a natural process, which is known as an age-related weight depletion. No weight depletion was observed in the group of animals that were treated with dimebon. The depletion in weight in the experimental group was observed only in the 23 month old animals, however, even then, their weight was higher compared to the animals in the control group. It should be noted, though, that the observed variation in weight was not statistically significant ($P>0.05$).

Vision Disturbances.

Vision disturbances, appearing as a development of cataract on one or both eyes, was observed in the control group of animals on the second month of the experiment. The amount of animals with cataract in this group was rapidly growing every month. The amount of animals that had cataract in the group receiving dimebon was significantly less ($P<0.05$, for 13 to 20 months old mice). Starting with the month 18, the amount of animals having cataract also increased in the experimental group. The comparative analysis between the control and experimental groups between months 18 through 21 was complicated, because many of the animals that had cataract in the control group died, while animals in the experimental group were still alive.

Skin and Hair Condition.

Starting from the first month of the experiment, animals with the disturbances in their skin-hair integument, in the form of bald spots or so-called alopecia, were observed. The size of bald spots in these animals was varied from 1 to 25% of the body surface. By the end of the experiment, same as in case with cataract, the amount of animals that had alopecia in the control group declined because of the death of animals, while animals in the experimental group were still alive.

The results suggest that dimebon statistically reliably decreases the probability of death in old animals. In addition, there is a statistically reliable evidence that there is a strong correlation between feeding old animals with dimebon and slowing of the development of non-fatal pathologies, such as loss of vision and alopecia. A decrease in weight, which is a valid characteristic of ageing, is significantly slower in a group receiving dimebon compared to the control group. Thus, simebon prolongs life and decreases the probability of non-fatal age-related pathologies. In other words, it improves the quality of life of old animals. All of the above suggests that dimebon, in addition to its ability to have a potential in a therapy of Alzheimer's disease is an effective geroprotector.

Example 10

The various new and non-obvious exemplary compounds (and new and non-obvious methods of making them) presented herein are believed to have dramatically improved functional in vitro and in vivo properties over an existing compound commonly known as dimebon. Among other things, the compounds presented herein are believed to have an improved half-life and/or sustainability within mammals (e.g. humans), representing a dramatic achievement for establishing and maintaining active, therapeutic, and/or pharmacologically effective amounts within mammals. Accordingly, data based upon dimebon may provide guidance for the various exemplary methods described herein.

Antihistamine Properties.

Because of the known antihistamine properties of dimebon, the various exemplary compounds described herein may also have similar properties, including acting as antagonists of $H_1$ and/or $H_3$ histamine receptors in mammals.

The $H_1$ receptor is a histamine receptor, and thus an important target for clinically important drugs, and is likely one of the most important receptors for modulating mammalian circadian cycles.

Histamine $H_1$ receptors are metabotropic G-protein-coupled receptors expressed throughout the body, specifically in smooth muscles, on vascular endothelial cells, in the heart, and in the central nervous system. The $H_1$ receptor is linked to an intracellular G-protein which activates phospholipase C and the phosphatidylinositol (PIP2) signalling pathway.

Histamine $H_3$ receptors are expressed in the central nervous system and to a lesser extent the peripheral nervous system, where they act as autoreceptors in presynaptic histaminergic neurons, and also control histamine turnover by feedback inhibition of histamine synthesis and release. The $H_3$ receptor has also been shown to presynaptically inhibit the release of a number of other neurotransmitters (i.e. it acts as an inhibitory heteroreceptor) including, but probably not limited to dopamine, GABA, acetylcholine, noradrenaline, and serotonin. This receptor has been proposed as a target for treating sleep disorders.

While various embodiments have been described above, it should be understood that they have been presented by way of example only, and not limitation. Thus, the breadth and scope of a preferred embodiment should not be limited by any of the above-described exemplary embodiments.

What is claimed is:

1. A compound or a pharmacologically acceptable salt thereof, which is selected from a group consisting of:
    5-[2-(5-fluoropyridin-3-yl)ethyl]-2-methyl-2,3,4,5-tetrahydro-1H-pyrido[4,3-b]indole;
    8-chloro-5-[2-(5-fluoropyridin-3-yl)ethyl]-2-methyl-2,3,4,5-tetrahydro-1H-pyrido[4,3-b]indole;
    8-bromo-5-[2-(5-fluoropyridin-3-yl)ethyl]-2-methyl-2,3,4,5-tetrahydro-1H-pyrido[4,3-b]indole;
    5-[2-(5-fluoropyridin-3-yl)ethyl]-8-methoxy-2-methyl-2,3,4,5-tetrahydro-1H-pyrido[4,3-b]indole;
    5-[2-(5-fluoropyridin-3-yl)ethyl]-2,6,8-trimethyl-2,3,4,5-tetrahydro-1H-pyrido[4,3-b]indole;
    6,8-difluoro-5-[2-(5-fluoropyridin-3-yl)ethyl]-2-methyl-2,3,4,5-tetrahydro-1H-pyrido[4,3-b]indole;
    5-[2-(5-fluoropyridin-3-yl)ethyl]-2-methyl-8-(trifluoromethyl)-2,3,4,5-tetrahydro-1H-pyrido[4,3-b]indole;
    5-[2-(5-fluoropyridin-3-yl)ethyl]-2-methyl-8-(trifluoromethoxy)-2,3,4,5-tetrahydro-1H-pyrido[4,3-b]indole;
    2-ethyl-5-[2-(5-fluoropyridin-3-yl)ethyl]-2,3,4,5-tetrahydro-1H-pyrido[4,3-b]indole;
    2-ethyl-5-[2-(5-fluoropyridin-3-yl)ethyl]-8-methyl-2,3,4,5-tetrahydro-1H-pyrido[4,3-b]indole;
    2-benzyl-5-[2-(5-fluoropyridin-3-yl)ethyl]-8-methyl-2,3,4,5-tetrahydro-1H-pyrido[4,3-b]indole;
    2-ethyl-8-fluoro-5-[2-(5-fluoropyridin-3-yl)ethyl]-2,3,4,5-tetrahydro-1H-pyrido[4,3-b]indole; and
    8-chloro-2-ethyl-5-[2-(5-fluoropyridin-3-yl)ethyl]-2,3,4,5-tetrahydro-1H-pyrido[4,3-b]indole.

2. A compound or a pharmacologically acceptable salt thereof, which is selected from a group consisting of:
    5-[2-(5-fluoropyridin-3-yl)ethyl]-2-iso-propyl-2,3,4,5-tetrahydro-1H pyrido[4,3-b]indole;
    5-[2-(5-fluoropyridin-3-yl)ethyl]-2,8-diethyl-2,3,4,5-tetrahydro-1H-pyrido[4,3-b]indole;
    8-fluoro-5-[2-(5-fluoropyridin-3-yl)ethyl]-2-iso-propyl-2,3,4,5-tetrahydro-1H-pyrido[4,3-b]indole;
    8-chloro-5-[2-(5-fluoropyridin-3-yl)ethyl]-2-iso-propyl-2,3,4,5-tetrahydro-1H-pyrido[4,3-b]indole;
    8-bromo-5-[2-(5-fluoropyridin-3-yl)ethyl]-2-ethyl-2,3,4,5-tetrahydro-1H-pyrido[4,3-b]indole;
    5-[2-(5-fluoropyridin-3-yl)ethyl]-8-methoxy-2-ethyl-2,3,4,5-tetrahydro-1H-pyrido[4,3-b]indole;
    5-[2-(5-fluoropyridin-3-yl)ethyl]-2-ethyl-6,8-dimethyl-2,3,4,5-tetrahydro-1H-pyrido[4,3-b]indole;
    6,8-difluoro-5-[2-(5-fluoropyridin-3-yl)ethyl]-2-ethyl-2,3,4,5-tetrahydro-1H-pyrido[4,3-b]indole;
    5-[2-(5-fluoropyridin-3-yl)ethyl]-2-ethyl-8-(trifluoromethyl)-2,3,4,5-tetrahydro-1H-pyrido[4,3-b]indole;
    5-[2-(5-fluoropyridin-3-yl)ethyl]-2-ethyl-8-(trifluoromethoxy)-2,3,4,5-tetrahydro-1H-pyrido[4,3-b]indole;
    2-tret-butyl-5-[2-(5-fluoropyridin-3-yl)ethyl]-2,3,4,5-tetrahydro-1H-pyrido[4,3-b]indole;
    2-iso-propyl-5-[2-(5-fluoropyridin-3-yl)ethyl]-8-methyl-2,3,4,5-tetrahydro-1H-pyrido[4,3-b]indole;
    2-tret-butyl-5-[2-(5-fluoropyridin-3-yl)ethyl]-8-methyl-2,3,4,5-tetrahydro-1H-pyrido[4,3-b]indole;
    2-tret-butyl-8-fluoro-5-[2-(5-fluoropyridin-3-yl)ethyl]-2,3,4,5-tetrahydro-1H-pyrido[4,3-b]indole;
    8-chloro-2-tret-butyl-5-[2-(5-fluoropyridin-3-yl)ethyl]-2,3,4,5-tetrahydro-1H-pyrido[4,3-b]indole;
    5-[2-(5-fluoropyridin-3-yl)ethyl]-2,8-diethyl-6-methyl-2,3,4,5-tetrahydro-1H-pyrido[4,3-b]indole;
    8-ethyl-5-[2-(5-fluoropyridin-3-yl)ethyl]-2-methyl-2,3,4,5-tetrahydro-1H-pyrido[4,3-b]indole;
    8-ethyl-5-[2-(5-fluoropyridin-3-yl)ethyl]-2,6-dimethyl-2,3,4,5-tetrahydro-1H-pyrido[4,3-b]indole;
    8-ethyl-5-[2-(5-fluoropyridin-3-yl)ethyl]-2-iso-propyl-2,3,4,5-tetrahydro-1H-pyrido[4,3-b]indole;
    8-ethyl-5-[2-(5-fluoropyridin-3-yl)ethyl]-2-iso-propyl-6-methyl-2,3,4,5-tetrahydro-1H-pyrido[4,3-b]indole;
    8-ethyl-5-[2-(5-fluoropyridin-3-yl)ethyl]-2-tret-butyl-2,3,4,5-tetrahydro-1H-pyrido[4,3-b]indole;
    8-ethyl-5-[2-(5-fluoropyridin-3-yl)ethyl]-2-tret-butyl-6-methyl-2,3,4,5-tetrahydro-1H-pyrido[4,3-b]indole;
    2-{5-[2-(5-fluoropyridin-3-yl)ethyl]-1,3,4,5-tetrahydro-2H-pyrido[4,3-b]indol-2-yl}ethanol;
    2-{5-[2-(5-fluoropyridin-3-yl)ethyl]-8-methyl-1,3,4,5-tetrahydro-2H-pyrido[4,3-b]indol-2-yl}ethanol; and
    2-{8-fluoro-5-[2-(5-fluoropyridin-3-yl)ethyl]-1,3,4,5-tetrahydro-2H-pyrido[4,3-b]indol-2-yl}ethanol.

* * * * *